United States Patent
Jain et al.

(10) Patent No.: US 10,172,517 B2
(45) Date of Patent: Jan. 8, 2019

(54) IMAGE-ANALYSIS FOR ASSESSING HEART FAILURE

(71) Applicant: Samsung Electronics Co., Ltd., Gyeonggi-Do (KR)

(72) Inventors: Jawahar Jain, Los Altos, CA (US); Cody Wortham, Mountain View, CA (US); James Young, Menlo Park, CA (US); Sajid Sadi, San Jose, CA (US); Pranav Mistry, Campbell, CA (US); Abhijit Z. Bendale, Sunnyvale, CA (US)

(73) Assignee: SAMSUNG ELECTRONICS CO., LTD, Gyeonggi-Do (KR)

( * ) Notice: Subject to any disclaimer, the term of this patent is extended or adjusted under 35 U.S.C. 154(b) by 0 days.

(21) Appl. No.: 15/436,920

(22) Filed: Feb. 20, 2017

(65) Prior Publication Data
US 2017/0245759 A1    Aug. 31, 2017

Related U.S. Application Data

(60) Provisional application No. 62/300,028, filed on Feb. 25, 2016, provisional application No. 62/300,024, (Continued)

(51) Int. Cl.
*G06K 9/00* (2006.01)
*A61B 5/00* (2006.01)
(Continued)

(52) U.S. Cl.
CPC .......... *A61B 5/0002* (2013.01); *A61B 5/004* (2013.01); *A61B 5/087* (2013.01); *A61B 5/165* (2013.01);
(Continued)

(58) Field of Classification Search
CPC .......... A61B 5/00; A61B 5/02; A61B 5/7275; A61B 5/0205; A61B 5/0082; A61B 5/113;
(Continued)

(56) References Cited

U.S. PATENT DOCUMENTS

| 5,144,949 A | 9/1992 | Olson |
| 6,077,222 A | 6/2000 | Lloyd et al. |

(Continued)

FOREIGN PATENT DOCUMENTS

| EP | 0559847 A1 | 9/1993 |
| EP | 1192971 A2 | 8/2001 |

(Continued)

OTHER PUBLICATIONS

Lee, J. et al., "Atrial Fibrillation Detection using a Smart Phone," In 34th Annual Int'l. Conf. of the IEEE Engineering in Medicine and Biology Society (EMBC), Sep. 1, 2012, pp. 1177-1180.
(Continued)

*Primary Examiner* — Amir Alavi
(74) *Attorney, Agent, or Firm* — Cuenot, Forsythe & Kim, LLC

(57) ABSTRACT

An apparatus for assessing heart failure can include an image sensor configured to capture image data of a patient, a sensor configured to capture sensor data for the patient, a memory configured to store the image data and the sensor data, and a processor coupled to the image sensor, the sensor, and the memory. The processor is configured to receive image data in response to detecting a biological condition from the sensor data, wherein the biological condition is indicative of psychophysiological health and cardiac health. The processor is further configured to detect a visual characteristic from the image data, wherein the visual characteristic is indicative of heart health, and, in response to
(Continued)

detecting the visual characteristic, provide an indication that the patient is experiencing a worsening of heart failure.

40 Claims, 11 Drawing Sheets

Related U.S. Application Data filed on Feb. 25, 2016, provisional application No. 62/299,960, filed on Feb. 25, 2016, provisional application No. 62/300,020, filed on Feb. 25, 2016, provisional application No. 62/300,038, filed on Feb. 25, 2016.

(51) Int. Cl.
    *A61B 5/087*     (2006.01)
    *A61B 5/16*     (2006.01)

(52) U.S. Cl.
    CPC .............. *A61B 5/44* (2013.01); *A61B 5/4842* (2013.01); *A61B 5/4875* (2013.01)

(58) Field of Classification Search
    CPC . A61B 5/0816; A61B 5/04011; A61B 5/0002; A61B 5/004; A61N 1/365
    See application file for complete search history.

(56) References Cited

U.S. PATENT DOCUMENTS

| | | | |
|---|---|---|---|
| 6,472,988 B1 | 10/2002 | Feld et al. | |
| 6,540,674 B2 | 4/2003 | Zadrozny | |
| 6,904,311 B2 | 6/2005 | Freeberg | |
| 7,142,920 B2 | 11/2006 | Scheiner et al. | |
| 7,853,455 B2 | 12/2010 | Brown | |
| 7,869,877 B2 | 1/2011 | Kadhiresan | |
| 7,877,277 B1 | 1/2011 | Petit et al. | |
| 7,974,708 B2 | 7/2011 | Daum et al. | |
| 8,719,214 B2 | 5/2014 | Stergiou et al. | |
| 8,738,133 B2 | 5/2014 | Shuros et al. | |
| 8,781,564 B2 | 7/2014 | Kinnunen | |
| 8,876,688 B2 | 11/2014 | Hyde et al. | |
| 8,897,522 B2 | 11/2014 | Mestha et al. | |
| 8,903,491 B2 | 12/2014 | Hopper et al. | |
| 8,956,290 B2 | 2/2015 | Gilley et al. | |
| 8,972,013 B2 | 3/2015 | Maschino | |
| 8,986,206 B2 | 3/2015 | Kim et al. | |
| 9,002,427 B2 | 4/2015 | Tupin, Jr. | |
| 9,020,185 B2 | 4/2015 | Mestha et al. | |
| 9,027,552 B2 | 5/2015 | Angelico et al. | |
| 9,035,778 B2 | 5/2015 | Howie et al. | |
| 9,070,267 B2 | 6/2015 | Hanson et al. | |
| 9,089,760 B2 | 7/2015 | Tropper et al. | |
| 9,106,307 B2 | 8/2015 | Molettiere et al. | |
| 9,128,305 B2 | 9/2015 | Honore et al. | |
| 9,132,275 B2 | 9/2015 | Yu et al. | |
| 9,161,698 B2 | 10/2015 | Zhang et al. | |
| 9,168,017 B2 | 10/2015 | Ward et al. | |
| 9,171,196 B2 | 10/2015 | Wang et al. | |
| 9,173,615 B2 | 11/2015 | Katra et al. | |
| 9,180,140 B2 | 11/2015 | Lundberg et al. | |
| 9,185,353 B2 | 11/2015 | Mestha et al. | |
| 9,204,836 B2 | 12/2015 | Bender et al. | |
| 9,220,440 B2 | 12/2015 | Addison et al. | |
| 9,232,894 B2 | 1/2016 | Tesanovic et al. | |
| 9,232,897 B2 | 1/2016 | Thakur et al. | |
| 9,232,910 B2 | 1/2016 | Alshaer et al. | |
| 9,247,884 B2 | 2/2016 | Yuen et al. | |
| 9,248,306 B2 | 2/2016 | Joo et al. | |
| 9,250,104 B2 | 2/2016 | Greiner et al. | |
| 9,262,772 B2 | 2/2016 | Stivoric et al. | |
| 9,265,477 B2 | 2/2016 | Yang et al. | |
| 9,268,908 B2 | 2/2016 | Ashdown et al. | |
| 9,286,789 B2 | 3/2016 | Park et al. | |
| 9,294,898 B2 | 3/2016 | Shikama et al. | |
| 2004/0006492 A1 | 1/2004 | Watanage | |
| 2005/0070809 A1 | 3/2005 | Acres | |
| 2006/0218007 A1 | 9/2006 | Bjorner et al. | |
| 2007/0024946 A1 | 2/2007 | Panasyuk et al. | |
| 2007/0185391 A1 | 8/2007 | Morgan | |
| 2007/0207437 A1 | 9/2007 | Sachdeva et al. | |
| 2008/0150714 A1 | 6/2008 | Bauer et al. | |
| 2009/0058660 A1 | 3/2009 | Torch | |
| 2009/0076343 A1* | 3/2009 | James | A61B 5/0006 600/301 |
| 2009/0271347 A1 | 10/2009 | Hyde et al. | |
| 2010/0249531 A1 | 9/2010 | Hanlon et al. | |
| 2010/0256512 A1* | 10/2010 | Sullivan | A61B 5/113 600/529 |
| 2010/0298899 A1 | 11/2010 | Donnellly et al. | |
| 2011/0295084 A1* | 12/2011 | Thakur | A61B 5/0205 600/301 |
| 2012/0010504 A1 | 1/2012 | Furlan | |
| 2012/0029936 A1 | 2/2012 | Hanoun | |
| 2012/0109243 A1* | 5/2012 | Hettrick | G06F 19/3418 607/17 |
| 2012/0157856 A1* | 6/2012 | An | A61B 5/024 600/484 |
| 2012/0253207 A1* | 10/2012 | Sarkar | A61B 5/0004 600/483 |
| 2012/0259649 A1 | 10/2012 | Mallon et al. | |
| 2013/0024212 A1 | 1/2013 | Atakhorrami et al. | |
| 2013/0079646 A1* | 3/2013 | Bhunia | A61B 5/686 600/481 |
| 2013/0197381 A1* | 8/2013 | Charlton | A61B 5/686 600/523 |
| 2013/0209977 A1 | 8/2013 | Lathan et al. | |
| 2013/0261479 A1 | 10/2013 | Kemppainen et al. | |
| 2013/0281798 A1 | 10/2013 | Rau et al. | |
| 2014/0006041 A1 | 1/2014 | Steinhauer et al. | |
| 2014/0051047 A1 | 2/2014 | Bender et al. | |
| 2014/0051941 A1 | 2/2014 | Messerschmidt | |
| 2014/0058745 A1 | 2/2014 | Ji et al. | |
| 2014/0061047 A1 | 3/2014 | Stich et al. | |
| 2014/0081432 A1 | 3/2014 | Kingon et al. | |
| 2014/0100822 A1 | 4/2014 | Hiltner | |
| 2014/0107500 A1 | 4/2014 | Stamatopoulos et al. | |
| 2014/0112559 A1 | 4/2014 | Freeman et al. | |
| 2014/0114147 A1 | 4/2014 | Romesburg | |
| 2014/0149465 A1 | 5/2014 | Kannan et al. | |
| 2014/0155773 A1 | 6/2014 | Stamatopoulos et al. | |
| 2014/0171776 A1 | 6/2014 | Lin et al. | |
| 2014/0172442 A1 | 6/2014 | Broderick et al. | |
| 2014/0228649 A1 | 8/2014 | Rayner et al. | |
| 2014/0243686 A1 | 8/2014 | Kimmel | |
| 2014/0267668 A1 | 9/2014 | Ignatovich et al. | |
| 2014/0371604 A1 | 12/2014 | Katra et al. | |
| 2015/0011361 A1 | 1/2015 | Boyette et al. | |
| 2015/0031965 A1 | 1/2015 | Visvanathan et al. | |
| 2015/0038854 A1* | 2/2015 | Zhang | A61B 5/7275 600/479 |
| 2015/0065825 A1 | 3/2015 | Utley et al. | |
| 2015/0065898 A1 | 3/2015 | Prstojevich et al. | |
| 2015/0099952 A1 | 4/2015 | Lain et al. | |
| 2015/0125832 A1 | 5/2015 | Tran | |
| 2015/0165271 A1 | 6/2015 | Sung-Lien et al. | |
| 2015/0202492 A1 | 7/2015 | Domansky et al. | |
| 2015/0213217 A1 | 7/2015 | Amarasingham et al. | |
| 2015/0269851 A1 | 9/2015 | Lee et al. | |
| 2015/0305683 A1 | 10/2015 | Friat et al. | |
| 2015/0317438 A1 | 11/2015 | Ingrassia, Jr. et al. | |
| 2015/0352147 A1 | 12/2015 | Lundberg et al. | |
| 2015/0359845 A1 | 12/2015 | Marban et al. | |
| 2015/0370993 A1 | 12/2015 | Moturu et al. | |
| 2015/0370994 A1 | 12/2015 | Madan et al. | |
| 2015/0374289 A1 | 12/2015 | Teller et al. | |
| 2015/0379477 A1 | 12/2015 | Junqua et al. | |
| 2016/0008957 A1 | 1/2016 | Kaur et al. | |
| 2016/0022193 A1 | 1/2016 | Rau et al. | |
| 2016/0045168 A1 | 2/2016 | Storer et al. | |
| 2016/0058336 A1 | 3/2016 | Blahnik et al. | |
| 2016/0063205 A1 | 3/2016 | Moturu et al. | |

(56) References Cited

U.S. PATENT DOCUMENTS

| | | |
|---|---|---|
| 2016/0091922 A1 | 3/2016 | Nazzaro et al. |
| 2017/0245805 A1 | 8/2017 | Jain et al. |
| 2017/0245808 A1 | 8/2017 | Jain et al. |
| 2017/0249437 A1 | 8/2017 | Jain et al. |

FOREIGN PATENT DOCUMENTS

| | | |
|---|---|---|
| EP | 1667578 A1 | 9/2004 |
| EP | 2739207 A1 | 6/2014 |
| EP | 2897067 A1 | 7/2015 |
| KR | 20000006830 A | 2/2000 |
| KR | 100545772 B1 | 1/2006 |
| KR | 20060092557 A | 8/2006 |
| KR | 20130010207 A | 1/2013 |
| WO | 9216258 A1 | 10/1992 |
| WO | 01008755 A1 | 2/2001 |
| WO | 02018019 A1 | 3/2002 |
| WO | 2013036853 A2 | 3/2013 |
| WO | 2014147496 A1 | 9/2014 |
| WO | 2015178637 A1 | 11/2015 |
| WO | 2016049425 A1 | 3/2016 |

OTHER PUBLICATIONS

"Web Cam Used to Detect Abnormal Heart Rhythm," [online] Reuters Health, In the Journal of mHealth, Oct. 15, 2014., vol. 1, No. 5, pp. 16-17, retrieved from the Internet: <https://www.joomag.com/magazine/the-journal-of-mhealth-vol-1-issue-5-oct-2014/0194692001413453930?page=18>.

Int'l. Appln. No. PCT/KR2016/014583A1, Int'l. Search Report and Written Opinion, dated Mar. 14, 2017, 11 pg.

Int'l. Appln. No. PCT/KR2017/002055, Int'l. Search Report and Written Opinion, dated May 29, 2017 11 pg.

Int'l. Appln. No. PCT/KR2017/002039,Int'l. Search Report, dated May 23, 2017, 3 pg.

Int'l. Appln. No. PCT/KR2017/002039, Written Opinion, dated May 23, 2017, 3 pg.

Int'l. Appln. No. PCT/KR2017/002055, Int'l. Search Report and Written Opinion, dated May 29, 2017, 13 pg.

Int'l. Appln. No. PCT/KR2017/002067, Int'l Search Report, dated May 29, 2017, 8 pg.

Int'l. Appln. No. PCT/KR2017/002067, Written Opinion, dated May 29, 2017.

Lauer, M.S., "Heart Rate Response in Stress Testing: Clinical Implications," In ACC Current Journal Review, vol. 10, No. 5, pp. 16-19, Oct. 31, 2001.

Melzer, C. et al, Predictors of Chronotropic Incompetence in the Pacemaker Patient Population, In Europace, vol. 8, No. 1, Jan. 2006. pp. 70-75.

Melzer, C. et al., "Chronotropic Incompetence: a Never-Ending Story," In Europace, vol. 12, No. 4, Apr. 2010, pp. 464-465.

Int'l. Appln. No. PCT/KR2017/002043, Int'l. Search Report, dated Apr. 28, 2017, 3 pg.

Int'l. Appln. No. PCT/KR2017/002043, Written Opinion, dated Apr. 28, 2017, 8 pg.

* cited by examiner

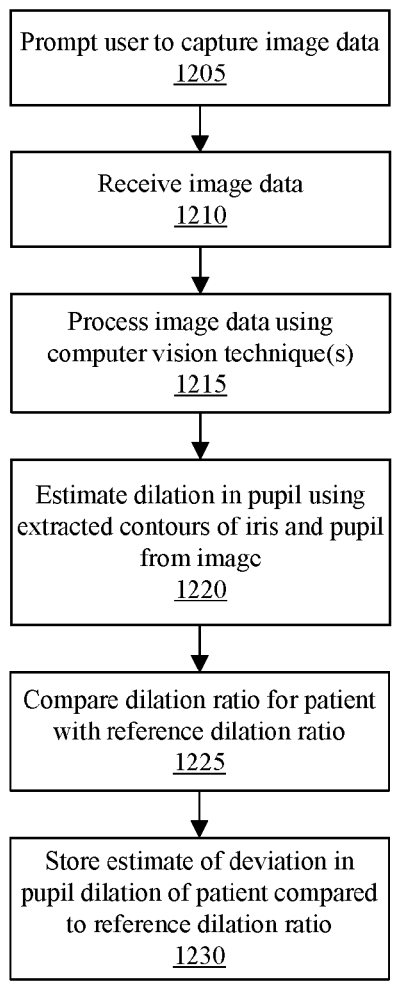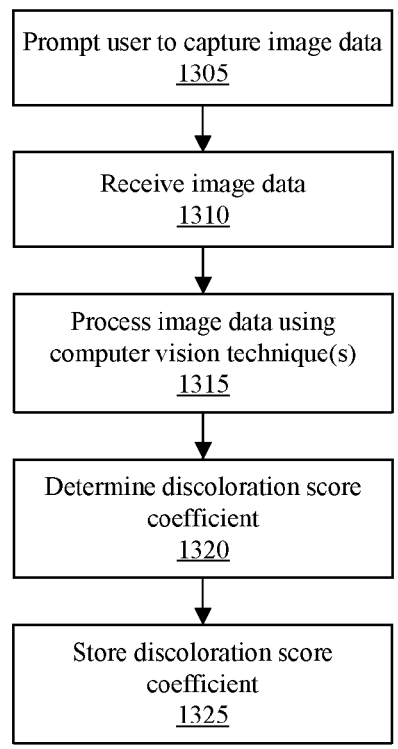
FIG. 12
FIG. 13

IMAGE-ANALYSIS FOR ASSESSING HEART FAILURE

CROSS-REFERENCE TO RELATED APPLICATIONS

This application claims the benefit of U.S. Provisional Patent Application No. 62/300,028 filed on Feb. 25, 2016, U.S. Provisional Patent Application No. 62/300,024 filed on Feb. 25, 2016, U.S. Provisional Patent Application No. 62/299,960 filed on Feb. 25, 2016, and U.S. Provisional Patent Application No. 62/300,020 filed on Feb. 25, 2016, and U.S. Provisional Patent Application No. 62/300,038 filed on Feb. 25, 2016, each being fully incorporated herein by reference.

TECHNICAL FIELD

This disclosure relates to assessing heart failure using sensor data and image analysis.

BACKGROUND

Exercise based cardiac rehabilitation has been shown to significantly reduce morbidity and mortality in cardiac patients including those patients suffering from heart failure. Exercise based cardiac rehabilitation is not always offered within a hospital setting due to various constraints. These constraints include, but are not limited to, limited availability of such programs, feasibility for the patient to participate, availability of secondary resources, etc.

Of those cardiac rehabilitation programs that do exist, exercise is generally prescribed from generic heart rate guidelines. Such is the case as many available cardiac rehabilitation programs are not operated in a hospital setting. In cases where physicians attempt to adjust generic heart rate guidelines to suit individual patients, the adjustments performed are also largely informed by generic guidelines. Any thresholds that are calculated, however, are subject to changes in the health of the patient.

Home-based cardiac rehabilitation programs have been shown to be a potential alternative for cardiac patients. Home-based cardiac rehabilitation programs provide benefits at reduced cost compared to more formal cardiac rehabilitation programs. Still, home-based cardiac rehabilitation programs provide little to no monitoring of risk factors and heart function in the patient. This lack of oversight is a significant source of concern for patient safety.

To illustrate the potential risk posed by lack of oversight, up to approximately a third of cardiac patients were found to have experienced an adverse event within a hospital setting during supervised cardiac rehabilitation. In more than half of these cases, changes to the treatments of the patients were required as a consequence of the event in order to ensure patient safety and reduce overall risk to the patients.

SUMMARY

One or more embodiments are directed to systems and/or apparatus for assessing heart failure. In one aspect, an apparatus includes an image sensor configured to capture image data of a patient, a sensor configured to capture sensor data for the patient, a memory configured to store the image data and the sensor data, and a processor coupled to the image sensor, the sensor, and the memory. The processor is configured to receive image data in response to detecting a biological condition from the sensor data, wherein the biological condition is indicative of psychophysiological health and cardiac health. The processor is further configured to detect a visual characteristic from the image data, wherein the visual characteristic is indicative of heart health, and, in response to detecting the visual characteristic, provide an indication that the patient is experiencing a worsening of heart failure.

One or more embodiments are directed to methods of assessing heart failure. In one aspect, a method can include processing, using a processor, sensor data for a patient obtained from a sensor to detect a biological condition. The biological condition is indicative of psychophysiological health and cardiac health. The method can include receiving, using the processor, image data in response to detecting the biological condition from the sensor data. The method can include detecting, using the processor, a visual characteristic from the image data, wherein the visual characteristic is indicative of heart health and, in response to detecting the visual characteristic, providing, using the processor, an indication that the patient is experiencing a worsening of heart failure.

One or more embodiments are directed to computer program products for assessing heart failure. In one aspect, a computer program product includes a computer readable storage medium having program code stored thereon. The program code is executable by a processor to perform executable operations. The executable operations can include processing sensor data for a patient obtained from a sensor to detect a biological condition. The biological condition is indicative of psychophysiological health and cardiac health. The executable operations can include receiving image data in response to detecting the biological condition from the sensor data and detecting a visual characteristic from the image data, wherein the visual characteristic is indicative of heart health. The executable operations can also include, in response to detecting the visual characteristic, providing an indication that the patient is experiencing a worsening of heart failure.

One or more embodiments are directed to systems and/or apparatus for assessing heart failure. In one aspect, the apparatus can include an image sensor configured to capture image data, a memory configured to store the image data, and a processor coupled to the image sensor and the memory. The processor is configured to generate a morphable model based upon image data for a selected part of a patient's body, receive a user specified deformation to the morphable model, wherein the deformation approximates an amount of pitting experienced by the patient for the selected part of the patient's body, and determine a measure of severity of edema experienced by the patient based upon the deformation to the morphable model.

One or more other embodiments are also directed to methods and computer program products relating to detection of heart failure and/or worsening of heart failure that include the various operations described within this disclosure.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more embodiments; however, the accompanying drawings should not be

FIG. 12 illustrates an example method of image analysis for pupil dilation.

FIG. 13 illustrates an example method of image analysis for skin color.

DETAILED DESCRIPTION

Figure 1:
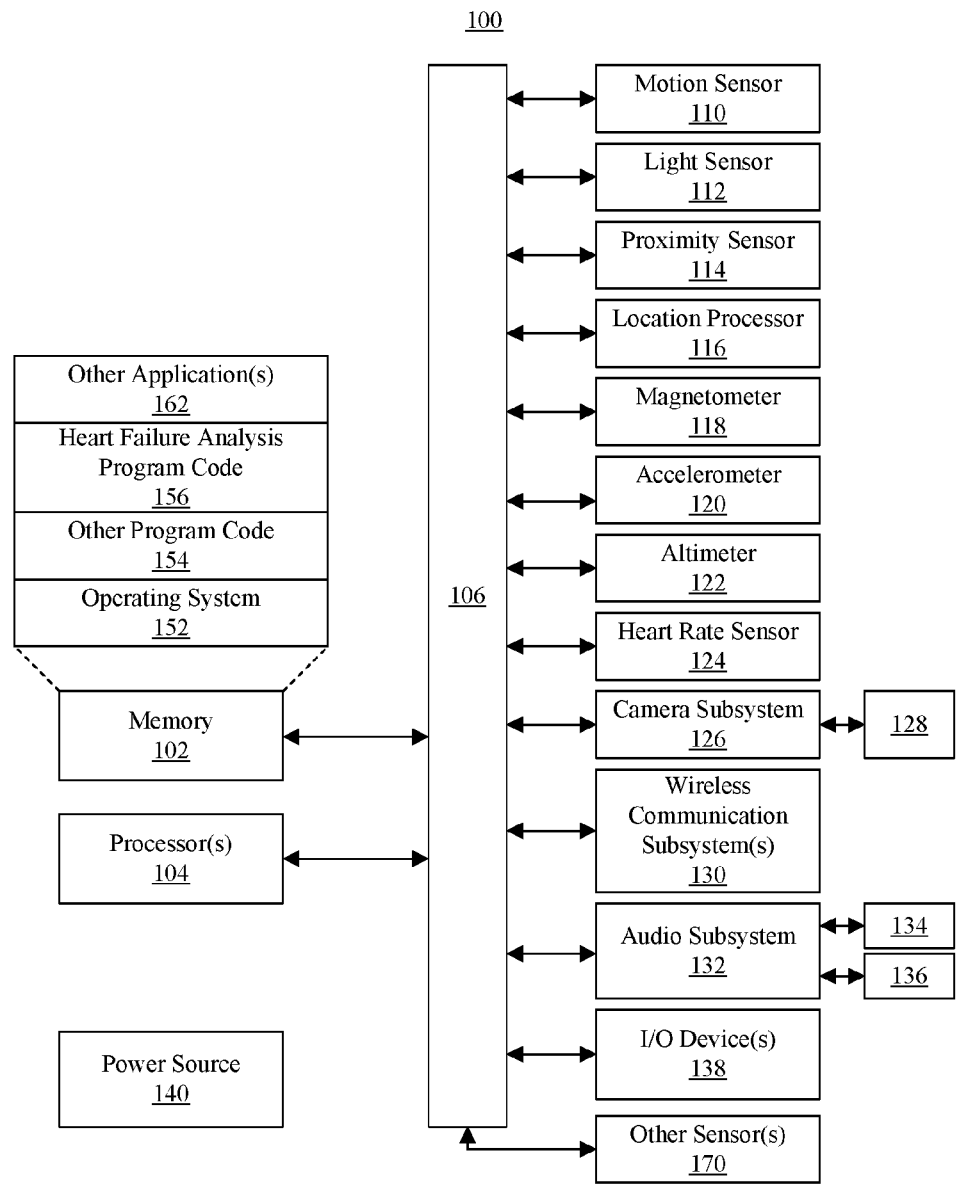
FIG. 1 illustrates an example architecture for a system.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to assessing heart failure in an individual using sensor data and image analysis. Available techniques for automated analysis of heart failure often generate false positives indicating that a patient is experiencing worsening heart failure when this is not the case. The example embodiments described within this disclosure are able to determine and/or detect worsening heart failure in a heart failure patient with increased accuracy thereby reducing the number of false positives generated and reducing the expense associated with attending to false positives.

The inventive arrangements described within this disclosure collect data from a patient using a variety of different sensors. The data may be continuously collected and analyzed in order to detect one or more biological conditions indicative of psychophysiological health and cardiac health. In response to detecting one or more of the biological condition(s), the system is configured to perform image analysis upon images and/or video of the patient. Image analysis may be performed to detect and/or quantity different visual characteristics. These visual characteristics may be indicative of pupil dilation, the presence of edema, cyanosis or skin discoloration (pale skin), and/or emotional state of the patient as may be indicated by facial analysis and/or other techniques disclosed herein. Based upon the image analysis performed, the system determines whether the patient is experiencing a worsening of heart failure. In response, to detecting a worsening of heart failure, the system is capable of undertaking one or more actions such as providing notifications to the patient or to medical providers as to the deteriorating state of the patient.

In another aspect, the system is capable of detecting potential states during cardiac rehabilitation where a patient may need to wait before continuing to exercise or where the patient should contact a medical care provider. These potential states may be detected by combining computer vision (e.g., image analysis) and machine learning methods with information from sensors. In addition, patient activity, context, and application-patient interaction may be used.

In another aspect, the system is capable of performing remote healthcare monitoring. In addition to assessing the various symptoms and/or conditions described above, the system is capable of analyzing and detecting a range of human emotions related to the patient's well-being. In one or more embodiments, the system may be implemented as a smartphone or other portable device. The camera within such a device may be used for purposes of capturing images and/or video. The image analysis performed may be used for purposes of assessing severity of heart failure.

The example embodiments described herein are able to assess heart failure, whether chronic or secondary to acute myocardial infarction. As noted, sensor data and image analysis is used. The example embodiments disclosed herein allow a medical practitioner to determine, with certitude, whether a patient is going through precipitation of an acute event, so that relevant emergency aid can be provided. The example embodiments also allow the patient to interact with the medical care provider to provide the medical care provider with a clinical evaluation of various anatomical sites, and a variety of pathologies, so that symptomatic relief can be provided or a relevant diagnosis can be made. In addition, the example embodiments provide patients with a tool for understanding abnormalities in concert with a clinical evaluation.

The example embodiments disclosed herein may be used to reduce readmission rates of heart failure patients within 30 days of discharge from a health care facility (e.g., a hospital). New health care directives under the ICD-9-CM code in the CMS (Centers for Medicare & Medicaid Services) Hospital Admissions Reduction Program for AMI (Acute mycocardial infarction), HF (Heart Failure), and pneumonia impose a penalty for readmissions of patients within 30 days of discharge under heart failure.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates an example architecture 100 for a system. Architecture 100 can include a memory 102, one or more processors 104 (e.g., image processors, digital signal processors, data processors, etc.), and interface circuitry 106. Memory 102, processor(s) 104, and/or interface circuitry 106 can be separate components or can be integrated in one or more integrated circuits. The various components in architecture 100, for example, can be coupled by one or more communication buses or signal lines (e.g., interconnects and/or wires). In one aspect, memory 102 may be coupled to interface circuitry 106 via a memory interface (not shown).

Sensors, devices, subsystems, and/or input/output (I/O) devices can be coupled to interface circuitry 106 to facilitate the functions and/or operations described herein including the generation of sensor data. The various sensors, devices, subsystems, and/or I/O devices may be coupled to interface circuitry 106 directly or through one or more intervening I/O controllers (not shown).

For example, motion sensor 110, light sensor 112, and proximity sensor 114 can be coupled to interface circuitry 106 to facilitate orientation, lighting, and proximity functions, respectively, of a system using architecture 100. Location sensor 116 (e.g., a GPS receiver) can be connected to interface circuitry 106 to provide geo-positioning sensor data. Electronic magnetometer 118 (e.g., an integrated circuit chip) can be connected to interface circuitry 106 to provide sensor data that can be used to determine the direction of magnetic North. Thus, electronic magnetometer 118 can be used as an electronic compass. Accelerometer 120 can be connected to interface circuitry 106 to provide sensor data that can be used to determine change of speed and direction of movement of a system in 3-dimensions using architecture 100. Altimeter 122 (e.g., an integrated circuit) can be connected to interface circuitry 106 to provide sensor data that can be used to determine altitude. Heart rate sensor 124 can be connected to interface circuitry 106 to generate sensor data and facilitate measurement of a heartbeat and the determination of a heart rate.

Camera subsystem 126 can be coupled to an optical sensor 128. Optical sensor 128 can be implemented using any of a variety of technologies. Examples of optical sensor 128 can include, but are not limited to, a charged coupled device (CCD), a complementary metal-oxide semiconductor (CMOS) optical sensor, etc. Camera subsystem 126 and optical sensor 128 can be used to facilitate camera functions, such as recording images and/or video clips (hereafter "image data"). For purposes of this disclosure, image data is a subset of sensor data.

Communication functions can be facilitated through one or more wireless communication subsystems 130. Wireless communication subsystems 130 can include, but are not limited to, radio frequency receivers and transmitters and/or optical (e.g., infrared) receivers and transmitters, and so forth. The specific design and implementation of wireless communication subsystem 130 can depend on the communication network(s) over which a system using architecture 100 is intended to operate.

For purposes of illustration, wireless communication subsystem(s) 130 may be designed to operate over one or more mobile networks (e.g., GSM, GPRS, EDGE), a WiFi network which may include a WiMax network, a short range wireless network (e.g., a Bluetooth network), and/or any combination of the foregoing. Wireless communication subsystem(s) 130 can implement hosting protocols such that system 100 can be configured as a base station for other wireless devices.

Audio subsystem 132 can be coupled to a speaker 134 and a microphone 136 to facilitate voice-enabled functions, such as voice recognition, voice replication, digital recording, and telephony functions. Audio subsystem 132 is capable of generating audio type sensor data. In one or more embodiments, microphone 136 may be utilized as a respiratory sensor.

I/O devices 138 can be coupled to interface circuitry 106. Examples of I/O devices 138 can include, but are not limited to, display devices, touch sensitive display devices, track pads, keyboards, pointing devices, communication ports (e.g., USB ports), network adapters, buttons or other physical controls, and so forth. A touch sensitive device such as a display screen and/or a pad is configured to detect contact, movement, breaks in contact, etc., using any of a variety of touch sensitivity technologies. Example touch sensitive technologies include, but are not limited to, capacitive, resistive, infrared, and surface acoustic wave technologies, as well as other proximity sensor arrays or other elements for determining one or more points of contact with a touch sensitive device. One or more of I/O devices 138 may be adapted to control functions of sensors, subsystems, and such of architecture 100.

Architecture 100 further includes a power source 140. Power source 140 is capable of providing electrical power to the various elements of architecture 100. In an embodiment, power source 140 is implemented as one or more batteries. The batteries may be implemented using any of a variety of different battery technologies whether disposable (e.g., replaceable) or rechargeable. In another embodiment, power source 140 is configured to obtain electrical power from an external source and provide power (e.g., DC power) to the elements of architecture 100. In the case of a rechargeable battery, power source 140 further may include circuitry that is capable of charging the battery or batteries when coupled to an external power source.

Memory 102 can include a random access memory (e.g., volatile memory) and/or non-volatile memory, such as one or more magnetic disk storage devices, one or more optical storage devices, and/or flash memory. Memory 102 can store operating system 152, such as LINUX, UNIX, a mobile operating system, an embedded operating system, etc. Operating system 152 may include instructions for handling basic system services and for performing hardware dependent tasks.

Memory 102 may also store other program code 154. Examples of other program code 154 may include instructions that facilitate communicating with one or more additional devices, one or more computers and/or one or more servers; graphic patient interface processing; sensor-related processing and functions; phone-related processes and functions; electronic-messaging related processes and functions; Web browsing-related processes and functions; media processing-related processes and functions; GPS and navigation-related processes and functions; security functions; camera-related processes and functions including Web camera and/or Web video functions; and so forth. Memory 102 may also store one or more other application(s) 162.

Memory 102 may store heart failure analysis program code 156. In one aspect, heart failure analysis program code 156 is adapted to facilitate detection of a worsening of heart failure as described herein. Heart failure analysis program code 156 is capable of analyzing sensor data, querying a patient for input, querying one or more external data sources for information as needed, and performing comparisons of sensor data, patient input, and/or data obtained from the external data sources with baseline information. Heart failure analysis program code 156 is also capable of performing image analysis as described herein. Further aspects of operations performed through execution of heart failure analysis program code 156 are described herein with reference to the remaining figures. Heart failure analysis program code 156 may interoperate with other program code 154, operating system 152, and/or other applications 162 to perform the operations described herein.

Memory 102 may also store various types of data (not shown) such as sensor data, baseline data, reference data, data obtained by way of received patient input(s), and/or data obtained by way of querying one or more external data sources.

The various types of instructions and/or program code described are provided for purposes of illustration and not limitation. The program code may be implemented as separate software programs, procedures, or modules. Memory 102 can include additional instructions or fewer instructions. Furthermore, various functions of architecture 100 may be implemented in hardware and/or in software, including in one or more signal processing and/or application specific integrated circuits.

Program code stored within memory 102 and any data items used, generated, and/or operated upon by a system utilizing an architecture the same as or similar to that of architecture 100 are functional data structures that impart functionality when employed as part of the system. Further examples of functional data structures include, but are not limited to, sensor data, data obtained via patient input, data obtained via querying external data sources, baseline information, reference data, predictive models, and so forth. A "data structure" refers to a physical implementation of a data model's organization of data within a physical memory. As such, a data structure is formed of specific electrical or magnetic structural elements in a memory. A data structure imposes physical organization on the data stored in the memory as used by a processor.

In one or more embodiments, one or more of the various sensors and/or subsystems described with reference to architecture 100 may be separate devices that are coupled or communicatively linked to architecture 100 through wired or wireless connections. For example, one or more or all of motion sensor 110, light sensor 112, proximity sensor 114, location sensor 116, magnetometer 118, accelerometer 120, altimeter 122, heart rate sensor 124, camera subsystem 126, audio subsystem 132, and so forth may be implemented as separate systems or subsystems that couple to architecture 100 by way of I/O devices 138 and/or wireless communication subsystem(s) 130.

For example, one or more of the sensors may be worn directly by the patient and provide data to architecture 100 via a wired or wireless connection. Examples of additional sensors that are not illustrated in FIG. 1, but which may be used and/or worn by a patient to provide sensor data to architecture 100 can include, but are not limited to electrocardiography (ECG) sensors, photoplethysmography (PPG) sensors, respiratory sensors, etc. These additional sensors are represented in FIG. 1 by "other sensors" block 170. In one or more embodiments, such sensors and/or subsystems are configured to generate sensor data that is stored in a memory external to architecture 100. In that case, architecture 100, e.g., processors 104, may access the sensor data for use and/or analysis as described herein.

Architecture 100 may include fewer components than shown or additional components not illustrated in FIG. 1 depending upon the particular type of system that is implemented. In addition, the particular operating system and/or application(s) and other program code included may also vary according to system type. Further, one or more of the illustrative components may be incorporated into, or otherwise form a portion of, another component. For example, a processor may include at least some memory.

While a system configured to perform the operations described herein may utilize architecture 100, architecture 100 is provided for purposes of illustration and not limitation. A system configured to perform the operations described herein may have a different architecture than illustrated in FIG. 1. The architecture may be a simplified version of architecture 100 and include a processor and memory storing instructions. The architecture may include one or more sensors as described herein. A system using architecture 100 or an architecture similar thereto is capable of collecting data using the various sensors of the system or sensors coupled thereto. Within this disclosure, data generated by a sensor is called "sensor data."

Examples of systems that may utilize architecture 100 or another computing architecture similar thereto to implement one or more of the example embodiments described herein may include, but are not to limited to, a smart phone or other mobile device, a wearable computing device (e.g., smart watch, fitness tracker, patch, etc.), a dedicated medical device, a computer (e.g., desktop, laptop, tablet computer, other data processing system, etc.), and any suitable electronic device capable of sensing and processing the sensor data. Furthermore, it will be appreciated that embodiments can be deployed as a standalone device or deployed as multiple devices in a distributed client-server networked system.

Figure 2:
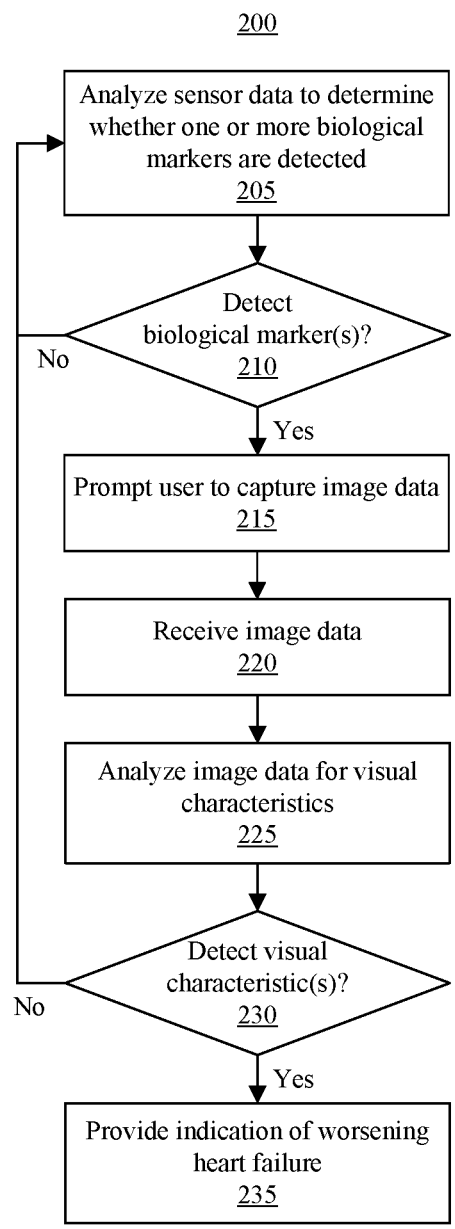
FIG. 2 illustrates a method of detecting a worsening of heart failure.

FIG. 2 illustrates a method 200 of detecting a worsening of heart failure. Method 200 is operative to detect a worsening of heart failure in a heart failure patient. Method 200 may be performed by a system having an architecture the same as or similar to the architecture described in connection with FIG. 1. For purposes of discussion, method 200 may begin in a state where a heart failure patient is using a system as described above and the system is continuously collecting sensor data.

FIG. 2 illustrates a multi-stage method for assessing heart failure in a patient. The first stage involves analysis of sensor data to detect one or more biological conditions. In one aspect, the first stage includes blocks 205 and 210. The second stage, which may be performed in response to detecting biological conditions in the first stage, involves image analysis. In one aspect, the second stage includes blocks 215, 220, 225, and 230.

In block 205, the system is capable of analyzing the sensor data. The system analyzes the sensor data to determine whether one or more biological conditions are detected therein. The biological conditions are indicative of cardiac health and psychophysiological health. Psychophysiological health refers to a branch of physiology that concerned with the relationship between mental (psyche) and physical (physiological) processes. Psychophysiological health is the scientific study of the interaction between mind and body.

Examples of biological conditions include, but are not limited to, chronotropic incompetence (CI), degradation in ventilation threshold, depression, and/or stress. In an aspect, the system detects at least one of the biological conditions in the patient. In another aspect, the system detects any two of the biological conditions occurring concurrently with one another in the patient. In another aspect, the system detects any three of the biological conditions occurring concurrently with one another in the patient. In another aspect, system detects each of the biological conditions occurring concurrently with one another in the patient. In still another aspect, the system detects at least one biological conditions relating to cardiac health (e.g., CI or degradation in ventilation threshold) and at least one of the biological conditions relating to mental health (e.g., depression or other mental state or stress).

In block 210, the system determines whether one or more biological conditions are detected. If so, method 200 continues to block 215. If not, method 200 loops back to block 205 to continue monitoring for the occurrence of one or more of the biological conditions.

In block 215, the system prompts the patient to capture image data. For example, in response to detecting one or more biological markers as described, the system prompts the patient to capture image data. The prompt may be a message displayed on the screen of the system, an audio message, and so forth. As noted, image data refers to images and/or video. The particular parts of the body for which image data is requested may be indicated by the system to the patient as part of the prompt that is provided. Further details relating to the image data are provided herein in connection with FIGS. 12, 13, 14, and 15.

In block 220, the system receives image data. For example, the system receives an image, images, and/or video taken by the patient. In an aspect, the system is configured to provide a prompt to indicate that the image is insufficient for purposes of analysis in a variety of different circumstances described herein in greater detail below. In an example, the system is capable performing image analysis to determine whether the image is of a minimum acceptable quality, e.g., having sufficient or a minimum amount of illumination. If not, the system may provide a prompt.

In block 225, the system analyzes the image data for one or more visual characteristics indicative of heart health. As illustrative examples, the system is capable of analyzing image data to detect visual characteristics indicative of edema, skin color and/or discoloration, and/or pupil dilation. In one or more embodiments, the system may perform image analysis, e.g., facial analysis, to detect emotional state in the patient. Further details relating to the image analysis performed and the visual characteristics that the system is capable of detecting are described herein in greater detail in connection with FIGS. 12, 13, 14, and 15.

In block 230, the system determines whether one or more of the visual characteristics are detected. If so, method 200 continues to block 235. If not, method 200 loops back to block 205 to continue processing.

In block 235, in response detecting the visual characteristic(s), the system provides a notification that the patient is experiencing a worsening of heart failure. In one aspect, the system provides the notification to the patient. For example, the notification may be provided as a message displayed on the screen of the system. In another aspect, the system is capable of contacting a medical service provider and/or providing a message to another system such as a system of a medical service provider. The notification may be an electronic mail, a text message, and so forth.

As discussed, one example of a biological condition that may be detected by the system is chronotropic incompetence. CI, broadly speaking, is the inability of the heart to increase its heart rate commensurate with increased activity or demand.

Figure 3:
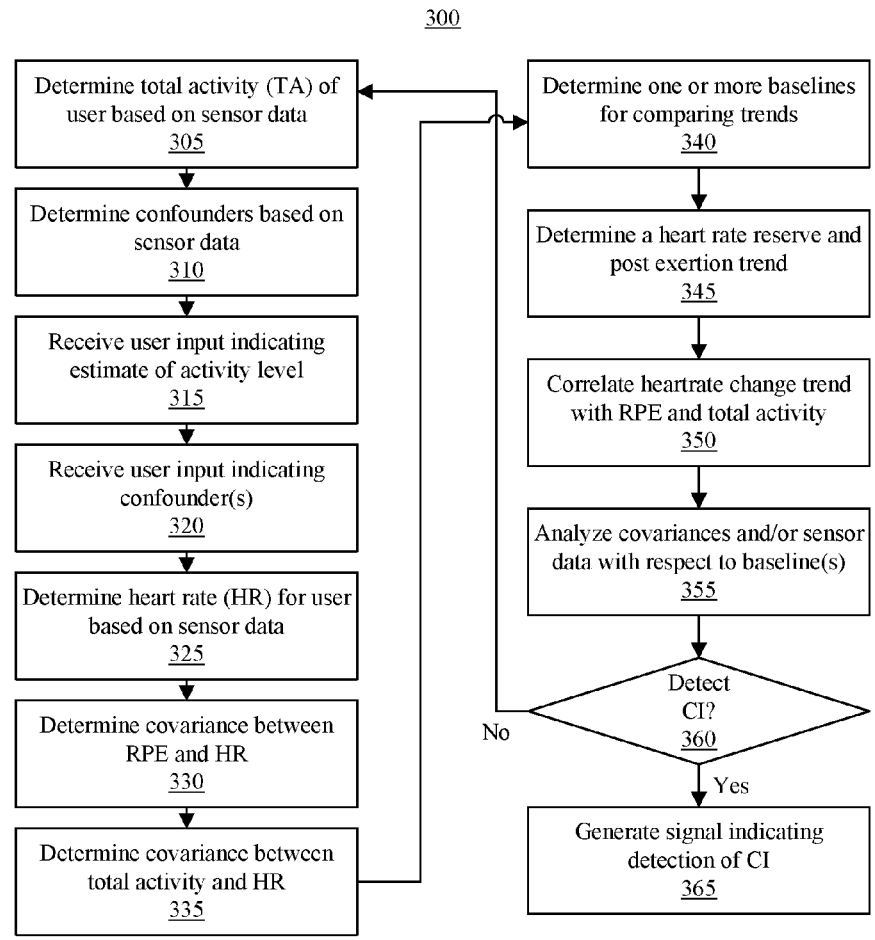
FIG. 3 illustrates an example method of detecting chronotropic incompetence (CI).

FIG. 3 illustrates an example method 300 of detecting CI. Method 300 may be performed by a system having an architecture the same as or similar to the architecture described in connection with FIG. 1. Method 300 may begin in a state where sensor data has been collected for the patient over time, e.g., a period of time, and is available for analysis. In one or more embodiments, the system collects the sensor data. In one or more other embodiments, one or more items of sensor data or all of the sensor data may be generated from other system(s) and/or device(s) and be read and/or processed by the system performing method 300.

In block 305, the system determines the total activity or "TA" of the patient based on sensor data. The system is capable of determining the total activity for the patient using accelerometer data. In one example, the system is capable of determining the total activity for the patient based on the power of the accelerometer output.

In block 310, the system optionally determines one or more confounders based on sensor data. A more detailed description of confounders and the automatic detection of such confounders by the system is provided herein in connection with FIG. 5.

In block 315, the system optionally receives a patient input indicating an estimate of activity level for the patient. In one or more embodiments, the estimate of the patient's activity level is a rating of perceived exertion or RPE. RPE is a measure of physical activity intensity level. RPE is based upon somatic or psychosomatic sensations related to difficulty of exertion that the patient experiences during physical activity which leads to symptoms such as increased heart rate, increased perspiration or breathing rate, increased sweating, muscle fatigue, and so forth. In any event, the RPE is generally considered a subjective measure of exertion on the part of the patient at least when received as a patient input in response to querying the patient. The system is capable of receiving a patient input specifying an RPE value.

In one or more embodiments, the RPE is expressed using the Borg scale. Table 1 below illustrates the scoring of RPE on the Borg scale.

TABLE 1

| Number | Level of Exertion |
|---|---|
| 6 | |
| 7 | Very, Very Light |
| 8 | |
| 9 | Very Light |
| 10 | |
| 11 | Fairly Light |
| 12 | |
| 13 | Somewhat hard |
| 14 | |
| 15 | Hard |
| 16 | |
| 17 | Very Hard |
| 18 | |
| 19 | Very, Very Hard |
| 20 | |

In one or more other embodiments, a different scale for measuring RPE may be used. In this regard, the inventive arrangements are not intended to be limited to using one particular scale for RPE. It should be appreciated that in an effort to ensure consistent results, patients may be trained in estimating activity level using an appropriate scale. For example, within a hospital setting, in a rehabilitation setting, or anywhere working with trained medical staff, the patient may be instructed in how to properly estimate activity level using the selected scale.

In one or more other embodiments, the estimate of activity level may be determined in an automated manner by the system without querying the patient for such information. In that case, querying the patient for an estimate of activity level need not be performed. The system can be adapted to determine an estimate of activity level, e.g., an RPE, from sensor data. In one example, the system is capable of determining or estimating activity level such as RPE by detecting respiration (ventilation) related sound from the patient related to exertion from audio sensor data. The system may estimate activity level or RPE by comparing progressive changes in the respiratory related sounds of the patient from audio sensor data that are indicative of exertion. Detecting respiratory sound is described herein in greater detail with reference to FIG. 4.

In block 320, the system optionally receives a patient input indicating one or more confounders. The system, for example, may query the patient for a list of confounders or to select those confounders applicable to the patient from a list of confounders presented to the patient. For example, the system may query the patient about medication intake. In one example, the system queries or asks the patient whether the patient is taking any beta blocker medication or any other drug that changes chronotropic nature of the function of the heart. Such medications and/or drugs may affect the measurements described below. As such, depending upon the medication and/or drugs indicated, the threshold for determining CI may be adjusted or changed.

In block 325, the system determines a heart rate (HR) for the patient based upon the sensor data. In block 330, the system determines a covariance COV(RPE, HR) between RPE and the HR. In block 335, the system determines a covariance COV(TA, HR) between the measured TA from block 305 and the HR of block 325. For example, referring to blocks 330 and 335, the system is capable of calculating covariances between any pair of the following: an HR time series, a TA time series, and RPE.

In block 340, the system determines one or more baseline cardiac health measures for comparing trends. In one or more embodiments, baseline cardiac health measures (or baselines) may be determined with the patient at rest and/or for one or more or each of the possible RPE values. The baselines may be stored for subsequent comparison with newly collected sensor data and/or patient input. Example baselines include, but are not limited to:

a covariance COV($RPE_{Rest}$, $HR_{Rest}$) between $RPE_{Rest}$ and $HR_{Rest}$;

a covariance between RPE and HR during exertion which can be denoted by COV($RPE_{exertion}$, $HR_{exertion}$);

a covariance COV($HR_{Rest}$, $TA_{Rest}$) between $HR_{Rest}$ and $TA_{Rest}$ at rest;

a covariance COV(HRR, $HR_D$) between HRR (heart rate recovery) and $HR_D$, where subscript "D" indicates deceleration trend (post-exertion) for HR with effort level and with total activity level as measured by sensors;

a covariance COV(EEE, RPE) between EEE (exercise energy expended), as may be measured using accelerometer activity, and RPE; and/or a respiration related sound recorded or observed at different RPE levels.

In one or more embodiments, a baseline cardiac health measure is determined from sensor data as described within this disclosure. For example, baseline cardiac health measures may be determined while the patient is at rest or in a known state. In one or more other embodiments, a baseline cardiac health measure is a reference state or data, e.g., predetermined or fixed data, that is specified by a physician, obtained from a standard, or the like and used for purposes of comparison as described herein.

In block 345, the system optionally determines an HRR and the HRR trend post-exertion. The system further is capable of correlating the HR change trend (e.g., the deceleration trend) with the RPE and with the measured TA of block 305. In one aspect, the system is capable of determining whether the heart rate recovery has a bi-exponential trend. For example, the system is capable of examining the logarithm of HRR for bi-exponentiality. The absence of a bi-exponential trend indicates CI. In block 350, the system optionally correlates HR change trend with RPE and total activity.

In block 355, the system is capable of analyzing one or more of the determined covariances and/or sensor data with respect to baselines. For example, the system is capable of detecting an anomaly such as a difference by more than a threshold from the baseline or an expected value. The lack of an expected covariance suggests detection of CI. In one embodiment, the system is capable of determining that an individual has CI responsive to determining that the covariance between energy expanded and RPE remains the same with the HR not being elevated. In other cases, where the covariance between EEE and RPE remains the same with EEE being low and RPE being high, the system is capable of determining that the individual has a reduced fitness level (e.g., not CI). The system is capable of calculating a cardiac health measure, including any of the covariances described herein, from sensor data to compare with a baseline cardiac health measure (e.g., a baseline covariance) to determine or estimate whether the patient has CI.

In one or more embodiments, the system is capable of adjusting the threshold for CI based upon medication intake or other confounders as determined in block 320. In one or more other embodiments, the threshold for CI is adjusted based upon one or more confounders detected within the sensor data from block 310. Examples of confounders include, but are not limited to, stress; sleep deprivation; tiredness; depression (mood); consumption of stimulants (caffeine, intoxicants etc.); any other drug that may have an effect on blood pressure and/or HR; state of health including fever, dehydration, or any other condition where HR and/or blood pressure, or other Autonomic Nervous System (ANS) markers can be reasonably expected to undergo significant change; and so forth. In one or more embodiments, the threshold for detecting CI is adjusted upward or downward based upon whether one or more of the confounders are detected within the sensor data. Confounders and the automated detection thereof from sensor data are discussed in further detail in connection with FIG. 5.

In one or more embodiments, the system is capable of accounting for confounders by computing the Relative Increase in HR (RIHR). RIHR is also called Increment % from HR at rest to Peak HR. RIHR may be calculated using the expression [(Peak HR−HR at Rest)/(HR at Rest)]×100.

In some cases, for individuals with CI that are taking beta blockers, a modified HR reserve may be used to account for confounders. The modified HR reserve (MHRR) may be calculated using the expression [(Increment % from HR at rest to peak HR)/(220−Age−HR at rest)]×100. Typically, HR reserve is calculated using the expression [(Peak HR−HR at rest)/(220−Age−HR at rest)]×100. The system further is capable of computing MHRR in one or more embodiments. It should be appreciated that HR reserve can also be calculated by estimating the Peak HR via any other varieties of accepted formulas that correlate expected peak HR with a person's age.

Using either RIHR or MHRR moves from an absolute calculation to a relative calculation for instances where HR may be depressed due to confounders. These relative calculations facilitate accurate detection of CI in instances where the HR increase is supposed to be larger if the HR at rest in the RIHR and/or MHRR expressions is modified to reflect or imply a baseline HR for a given instance. The system, for example, may calculate a baseline HR (e.g., the HR at rest) by measuring HR for an appropriate period of rest preceding the given exercise at a reasonably close time interval.

Using the RIHR and/or MHRR, CI detection may be performed subject to any confounders. It should be appreciated that the techniques described herein may be further modified to account for one or more confounders responsive to determining an approximation of the impact the confounder may have. For example, if the HR of an individual is typically elevated by 5 beats per minute (BPM) after caffeine consumption, then even without determining the baseline HR for a given instance, the HR may be selected from historical data. The system is capable of adding the 5 BPM to the historical HR to account for the caffeine consumption.

In block 360, the system determines whether one or more indicators of CI are detected. If so, method 300 proceeds to block 365. If not, method 300 may loop back to block 305 to continue processing. In block 365, the system generates a signal or notification that is output indicating that CI is detected. In one or more embodiments, responsive to detecting CI, the system is capable of providing an indication to a remote system. For example, the system is capable of providing a message or indication to a healthcare provider server based on the computed information.

While the above description is described in the context of computing covariance, alternative embodiments can use other similarity measures or dissimilarity measures, such as correlation or distance functions. Further, one or more or each of the calculations described in connection with FIG. 3 can be contextual. For example, the CI of a patient may be different in morning vs. in evening due to the circadian rhythm of various hormones secreted by the patient's endocrine system. In this regard, the CI threshold that is used may be varied according to context such as morning vs. evening.

Figure 4:
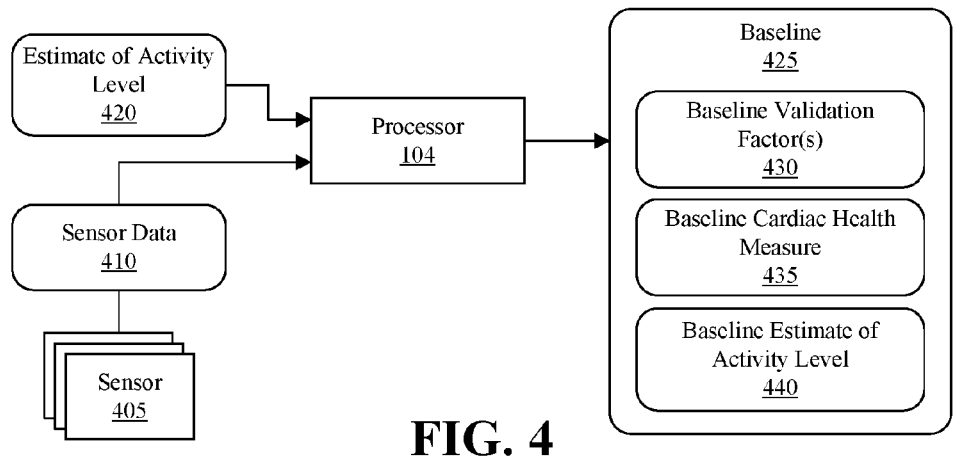
FIG. 4 illustrates an example of baseline generation for CI detection.

FIG. 4 illustrates an example of baseline generation for CI detection. Baseline generation may be performed at any of a variety of different times in order to establish one or more baselines for purposes of detecting CI in a patient. In one or more embodiments, baseline generation may be performed as part of an intake or onboarding process of a rehabilitation program. For example, a patient may be asked to perform one or more tasks, activities, or exercises. During that time, baseline 425 may be generated or otherwise determined. The baselines determined may be stored in the patient's system for purposes of later comparison.

As shown, one or more sensors 405 are capable of generating sensor data 410. Example sensors 405, as discussed with reference to FIG. 1, include, but are not limited to, an accelerometer, a heart rate sensor, a microphone, and so forth. Sensor data 410 is generated over a period of time. Accordingly, for the various values and/or quantities described, it should be appreciated that sensor data 410 includes a time series of such data. Sensor data 410 may be stored in a memory (not shown). As such, processor 104 may access (read and/or write) sensor data 410.

Processor 104 is also capable of receiving an estimate of activity level (EAL) 420 for the patient. EAL 420 may be provided by way of a received patient input. As noted, a system may query a patient for EAL 420. In another aspect, EAL 420 may be entered by the patient or an administrator responsive to asking the patient. As discussed, in one or more embodiments, EAL 420 is a rating of perceived exertion or RPE.

Processor 104 is capable of operating on sensor data 410 and EAL 420 to generate a baseline 425. In the example of FIG. 4, baseline 425 includes a baseline cardiac health measure 435 and baseline EAL 440. Processor 104 is capable of determining a cardiac health measure for the patient from sensor data 410 as generated by a sensor at or about the time that EAL 420 is received. Processor 104 stores the determined cardiac health measure as baseline cardiac health measure 435 in association with EAL 420 as part of baseline 425. EAL 420, when stored as part of baseline 425, is referred to as the "baseline EAL" 440.

In one or more embodiments, the baseline cardiac health measure is HR. In one or more other embodiments, the baseline cardiac health measure is one or more of the covariances described herein. In one or more other embodiments, the baseline cardiac health measure is one or more or a combination of HR and one or more of the covariances.

In one or more embodiments, processor 104 is capable of determining one or more baseline validation factors 430 from sensor data 410 for the time period within sensor data 410 for which baseline cardiac health measure 435 is determined. A "validation factor," as defined herein, for example, is one or more items of data determined from sensor data 410 other than items of sensor data used to determine baseline cardiac health measure 435, that is used to validate an EAL received from the patient. Appreciably, the time and/or time period for which a baseline validation factor 430 is determined for baseline 425 is the same time and/or time period for which baseline cardiac health measure 435 and baseline EAL 440 are determined for baseline 425.

One example of a validation factor, including a baseline validation factor, is TA. TA, which indicates energy expended by the patient, can be measured by accelerometer data that is included in sensor data 410. TA may be determined as previously described herein with reference to FIG. 3, for example. Processor 104 operates on accelerometer data to measure the energy expended, e.g., an amount of work for a given time or period of time, performed by the patient. In one or more embodiments, processor 104 is configured to include or read additional attributes of the patient such as height, weight, and age in order to more accurately calculate the expended energy of the patient as a baseline validation factor 430.

Another example of a validation factor, including a baseline validation factor, is respiratory sound indicating exertion. The respiratory sound may indicate a level of exertion for a patient indicating a level of difficulty. The microphone generates audio data that is included in sensor data 410. Processor 104 operates on the audio data to measure respiratory indications for exertion for a given time or period of time, for the patient. For example, processor 104 is capable of detecting breathing sounds (e.g., breath, wheezing, coughing, etc.) within the audio data and determining the characteristics of the breathing sounds as a baseline validation factor 430. The respiratory sound may be analyzed for different RPE to determine baselines for the different RPE.

Accordingly, baseline validation factor(s) 430 may be stored with baseline cardiac health measure 435 and baseline EAL 440 within baseline 425. By storing baseline validation factor(s) 430 as part of baseline 425, when baseline 425 is later used for purposes of evaluating cardiac health of the patient, newly determined validation factors may be compared with baseline validation factors 430 for a given EAL and/or cardiac health measure. The validation process is described in greater detail with reference to FIG. 5.

In the example of FIG. 4, while one baseline is illustrated, it should be appreciated that the operations described may be performed one or more additional times in order to generate further baselines. In one example, a baseline may be generated for one or more or for each possible value of the estimate of activity level or RPE. Referring to Table 1, for example, a baseline may be generated for each possible score for the RPE from 6 to 20.

Figure 5:
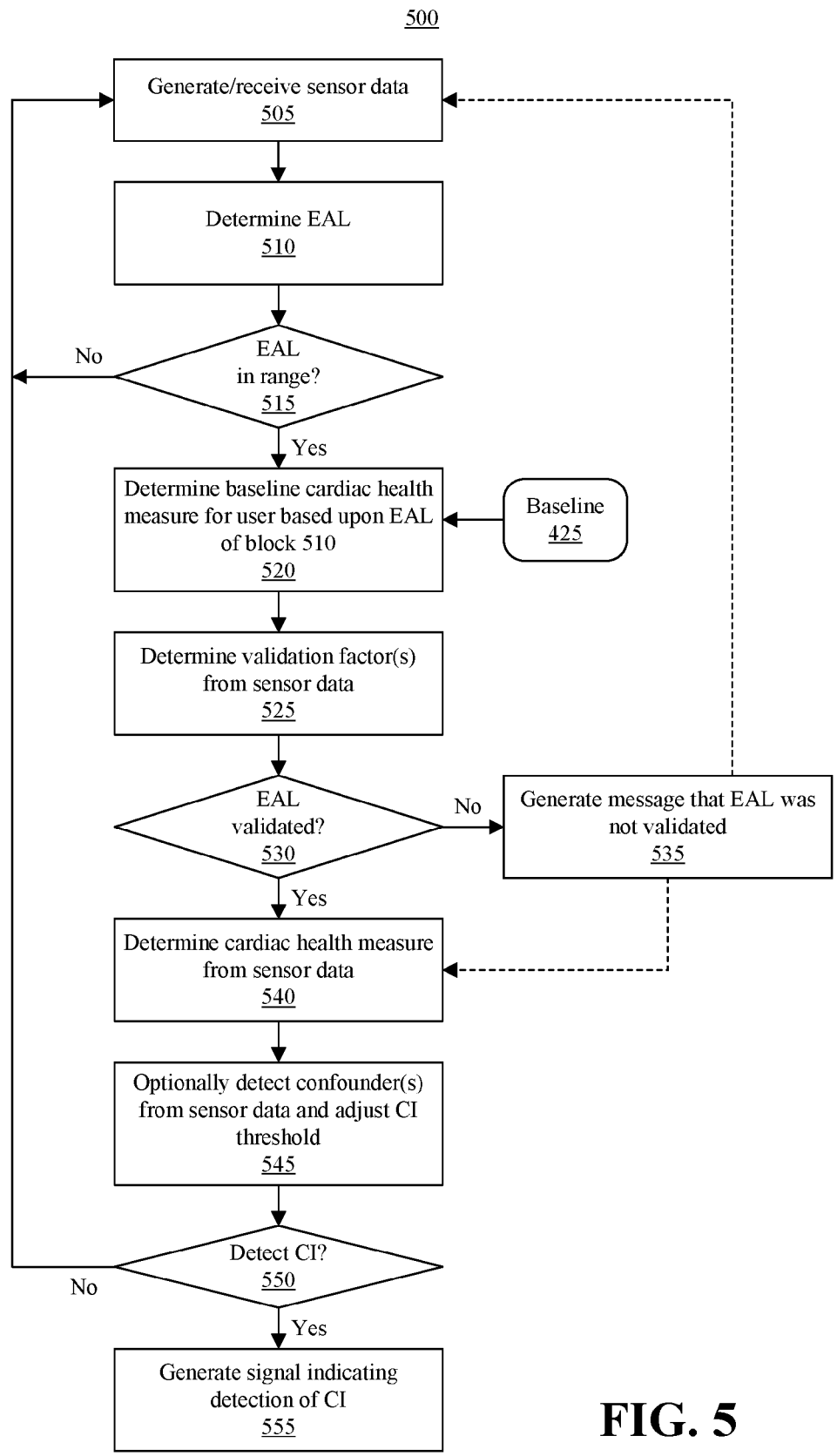
FIG. 5 illustrates is another example method of detecting CI.

FIG. 5 illustrates is another example method 500 of detecting CI. Method 500 may be performed by a system having a computing architecture the same as or similar to the architecture as described in connection with FIG. 1. Method 500 may begin in a state where one or more baselines as described herein with reference to FIGS. 3 and 4 are generated and stored. The baselines are available for use by the system in detecting CI.

In block 505, the system generates or receives sensor data. As noted, in one or more embodiments, the system collects the sensor data. In one or more other embodiments, one or more items of sensor data or all of the sensor data may be generated from other system(s) and/or device(s) and be read or received by the system performing method 500. In block 510, the system determines an EAL. In one or more embodiments, the system queries the patient for an EAL. The system receives a patient input specifying the EAL. In one or more other embodiments, the system is capable of estimating an EAL based upon respiratory sounds as previously described.

In block 515, the system determines whether the EAL is in a defined range. If so, method 500 continues to block 520. If not, method 500 loops back to block 505 to continue processing. In one or more embodiments, the EAL must be within a particular range in order to detect CI. In one example, the range is an RPE of 13 or 14. In that case, if the EAL specifies an RPE of 13 or 14, method 500 continues to block 520. If not, method 500 loops back to block 505 to continue processing.

In block 520, the system determines the baseline cardiac health measure for the patient based upon the EAL determined in block 510. For example, the system uses the EAL determined in block 510 and locates a matching baseline EAL within the baselines. As discussed with reference to FIG. 4, for example, each baseline stores a baseline EAL. If, for example, the EAL of block 510 is an RPE value of 13, the system looks up the baseline having a baseline EAL with an RPE value of 13. If, for example, the EAL of block 510 is an RPE value of 14, the system looks up the baseline having a baseline EAL with an RPE value of 14. For purposes of discussion, the system is capable of looking up baseline 425 using the EAL determined in block 510 as the baseline EAL and determining the baseline cardiac health measure from baseline 425. As noted, in one or more embodiments, the baseline cardiac health measure is HR, but may be or include one or more of the covariances described.

In block 525, the system is capable of determining one or more validation factors from the sensor data. The validation factors may be determined for the same time and/or same period of time to which the EAL determined in block 510 corresponds. For example, the system is capable of determining the validation factor of activity level from accelerometer sensor data and/or characteristics of respiratory sound indicating exertion from audio sensor data.

In block 530, the system is capable of validating the EAL received in block 510. In one or more embodiments, the system validates the EAL of block 510 by comparing one or more of the validation factors determined in block 525 with the corresponding baseline validation factor(s), e.g., validation factor(s) of the same type, from the baseline used to determine the baseline cardiac health measure. For example, the system may compare one or more of the validation factors determined in block 525 using current sensor data with the stored baseline validation factor(s) 430 of baseline 425.

As an illustrative example, the system may validate the EAL of block 510 by determining that the characteristics of respiratory sound indicating exertion determined in block 525 are within a predetermined threshold of, or match, baseline characteristics of respiratory sound indicating exertion specified in baseline validation factor(s) 430. As another illustrative example, the system may validate the EAL of block 510 by determining that the TA determined in block 525 is within a predetermined threshold or amount of a baseline TA specified in baseline validation factor(s) 430.

In still another illustrative example, the system may validate the EAL of block 510 by determining that the characteristics of respiratory sound determined in block 525 is/are the same as or similar to the characteristics of respiratory sound specified in baseline validation factor(s) 430 and that the total activity determined in block 525 is within a predetermined threshold or amount of a baseline total activity specified in baseline validation factor(s) 430.

In one or more embodiments, where the EAL is determined automatically from respiratory sound, the system may utilize a validation factor other than respiratory sound to perform validation.

Block 530 ensures that the EAL provided by the patient is consistent. In the event that the patient begins to provide inconsistent EALs, one or more of the validation factors will likely mismatch the baseline validation factors. For example, in the case where the patient over estimates the EAL, the validation factors will likely be lower than the baseline validation factors obtained from baseline 425, e.g., lower than the predetermined threshold or amount.

In any case, if the EAL is validated, method 500 may continue to block 540. If the EAL is not validated, method 500 may proceed to block 535. In block 535, the system may generate a message or notification that the EAL was not validated or that validation was not successful. In one or more embodiments, after block 535, method 500 may loop back to block 505 to continue processing. In one or more other embodiments, after block 535, method 500 may continue to block 540. For example, method 500 may continue to block 540 to detect CI despite the unsuccessful validation of the EAL. In that case, where CI is detected, the signal indicating detection of CI in block 555 may further indicate that while CI is detected, validation of the EAL was unsuccessful.

In block 540, the system is capable of determining a cardiac health measure for the patient from the sensor data. In one embodiment, the cardiac health measure is HR. The system is capable of determining the HR for the patient from the sensor data for the same time or same time period as the EAL received in block 520. In one or more other embodiments, the cardiac health measure is one or more covariances and/or a combination of HR and one or more covariances.

In block 545, the system optionally detects one or more confounders from the sensor data and adjusts a CI threshold. In one or more embodiments, the system is capable of detecting one or more confounders from the sensor data. Responsive to detecting a confounder in the sensor data, the system adjusts the CI threshold. In one or more embodiments, the CI threshold specifies how far the patient's HR, as determined in block 540, must be from a baseline HR (e.g., the baseline cardiac health measure) of block 520 for the system to detect CI. The CI threshold may be expressed as a percentage, a predetermined amount, or the like.

In one example, the system is capable of detecting, from the sensor data, the confounder of sleep deprivation. For example, the system is capable of measuring sleep of the patient using HR data and accelerometer data. The system is capable of determining the amount of time that the patient sleeps and comparing the amount of time spent sleeping with a baseline amount of time (whether personal to the patient or a generalized baseline determined across one or more other patients) to determine sleep deprivation for the patient. The system is capable of determining a measure of sleep deprivation expressed as a confounding factor.

In another example, the system is capable of detecting, from the sensor data, the confounder of stress. When under stress, for example, the patient's ANS arousal and valence are typically in the second quadrant of the Circumplex Model of Emotions, which can be determined by HR and HR variability (HRV) analysis where both trend down at the same time. In one embodiment, the system is capable of using HR and/or HRV to determine whether the patient is under stress and/or the amount of stress. For example, the system is capable of determining whether the patient is subject to stress and whether the amount of stress exceeds a baseline amount of stress based upon HR (e.g., energy) and HRV (e.g., mood) of the patient both being low (e.g., below a baseline for HR and/or a baseline for HRV) at the same time and/or remaining low (concurrently) for at least a minimum amount of time. The baseline may be specific to the patient or generalized across one or more different patients. Responsive to determining that the HR and HRV both are low for at least the minimum amount of time, for example, the system determines that the patient is experiencing stress. A measure of stress may be expressed as a confounding factor.

Responsive to detecting one or more of the confounding factors, the system adjusts the CI threshold. For example, the system increases the CI threshold. In one or more embodiments, the system increases the CI threshold a predetermined amount or percentage for each confounder detected. The system is further capable of increasing the CI threshold based upon the amount of one or more or each of the confounders detected. In one or more other embodiments, the system increases the CI threshold only responsive to determining that the, or each, confounder, while detected for the time or time period corresponding to the EAL received in block 510, was not present for the determination of the baseline HR.

In one or more other embodiments, the system is capable of using recent exertion history of the patient into account. As an illustrative example, if the patient has endured significant exertion in comparison to the patient's baseline level of exertion in a preceding time period that is sufficiently close to the time period being evaluated for CI, the patient is likely tired. As such, the patient is likely to indicate a high RPE despite the effort level for that given instance or period of time not really being high. Thus, in one or more embodiments, the system is capable of excluding instances of higher than baseline level of exertion that occur within a threshold or predetermined amount of time of an earlier period or instance of higher than baseline level of exertion from consideration in CI detection.

In block 550, the system determines whether CI is detected for the patient. In one or more embodiments, the system compares the HR determined in block 540 with the baseline HR determined in block 520. The system is capable of determining whether the HR is within the CI threshold of the baseline HR. In one example, the CI threshold is 80% of the baseline HR. If the HR is within the threshold or predetermined amount of the baseline HR, the system does not detect CI for the patient. Accordingly, method 500 may loop back to block 505. If the HR is not within the threshold or predetermined amount of the baseline HR, the system detects CI for the patient. In that case, method 500 continues to block 555.

In some cases, the system is configured to adjust the CI threshold. In one or more embodiments, the system is capable of measuring the fraction of HR reserve achieved after exercise. In that case, where the patient is starting with a higher HR than the patient's HR at rest, rather than using HR at rest, the system may compute the fraction of HR increase achieved by using the HR (during an inactive period) immediately prior to the period of exercise.

In other cases, the HR increase experienced by a patient may be affected by stress, a medical condition, and/or a medication. These effects may be determined by using a circadian baseline of the patient that is annotated with events and times. The circadian baseline, for example, may indicate events such as ingestion of caffeine and/or medication and times. Stress may be detected automatically. In one or more embodiments, the system is capable of receiving data indicating stress, medical condition, and/or medication from a medical provider and/or medical provider system.

In block 555, the system generates a signal or notification that is output indicating that CI is detected. In one or more embodiments, responsive to detecting CI, the system is capable of providing an indication to a remote system. For example, the system is capable of providing a message or indication to a healthcare provider server based on the computed information.

Referring to FIGS. 3 and 5, based upon the above calculations such as the presence and/or lack of covariance and/or the comparisons described, the system is capable of not only detecting CI, but also of detecting or determining improvement in CI. Improvement in CI can be a significant marker of improved health, and reduced mortality and morbidity. Conversely, worsening CI can imply a greater risk of mortality and morbidity and thus requires additional and appropriate clinical attention from the caretaking staff.

In one or more other embodiments, additional sensors may be incorporated to provide measurements that, if available, may be used as validation factors and/or to detect confounders. For example, if EEG and/or ECG data may be used to detect confounders. Visual images and/or video as may be obtained from a camera sensor may be used to aid in detecting sleep deprivation.

In an embodiment, the CI techniques described herein are implemented as a feature within a wearable device and/or smartphone. In one aspect, data may first be validated by a medical professional to validate or ensure accuracy of any CI estimation performed by the system. The medical professional may be a doctor or other individual with expertise in diagnosing and/or recognizing CI, cardiac conditions, etc. For example, the data and/or CI estimation may be validated by a doctor at a hospital or other medical facility where the doctor/medical professional uses clinical acumen and/or any associated testing. The validation may be performed using, or along, a scale of "quality of estimation." In one example, the scale for quality of estimation may range from A+ to D−, where A+ indicates a most believable and robust estimation. Once an estimate is obtained for a patient, going forward, the significance of any feedback about health including any alarm generated by the system may be interpreted accordingly.

In another embodiment, the "quality of estimation" may be generalized to additional patients, e.g., all patients, having a profile similar to the profile of the patient. For example, the relevant guidelines may be programmed on the system prior to sale or availability of the system. Once a system for a patient has collected sufficient data for the patient, based upon the patient's bio-markers and historic profile, the system is capable of performing the CI (or fitness) interpretation accordingly.

As discussed, another example of a biological condition that may be detected by the system is a deterioration in ventilation threshold. Ventilation threshold generally refers to the point at which a transition from moderate sustainable exercise to heavy exercise occurs for an individual. Ventilation threshold is effectively the transition point between an aerobic metabolism and an anaerobic metabolism.

Figures 6, 7:
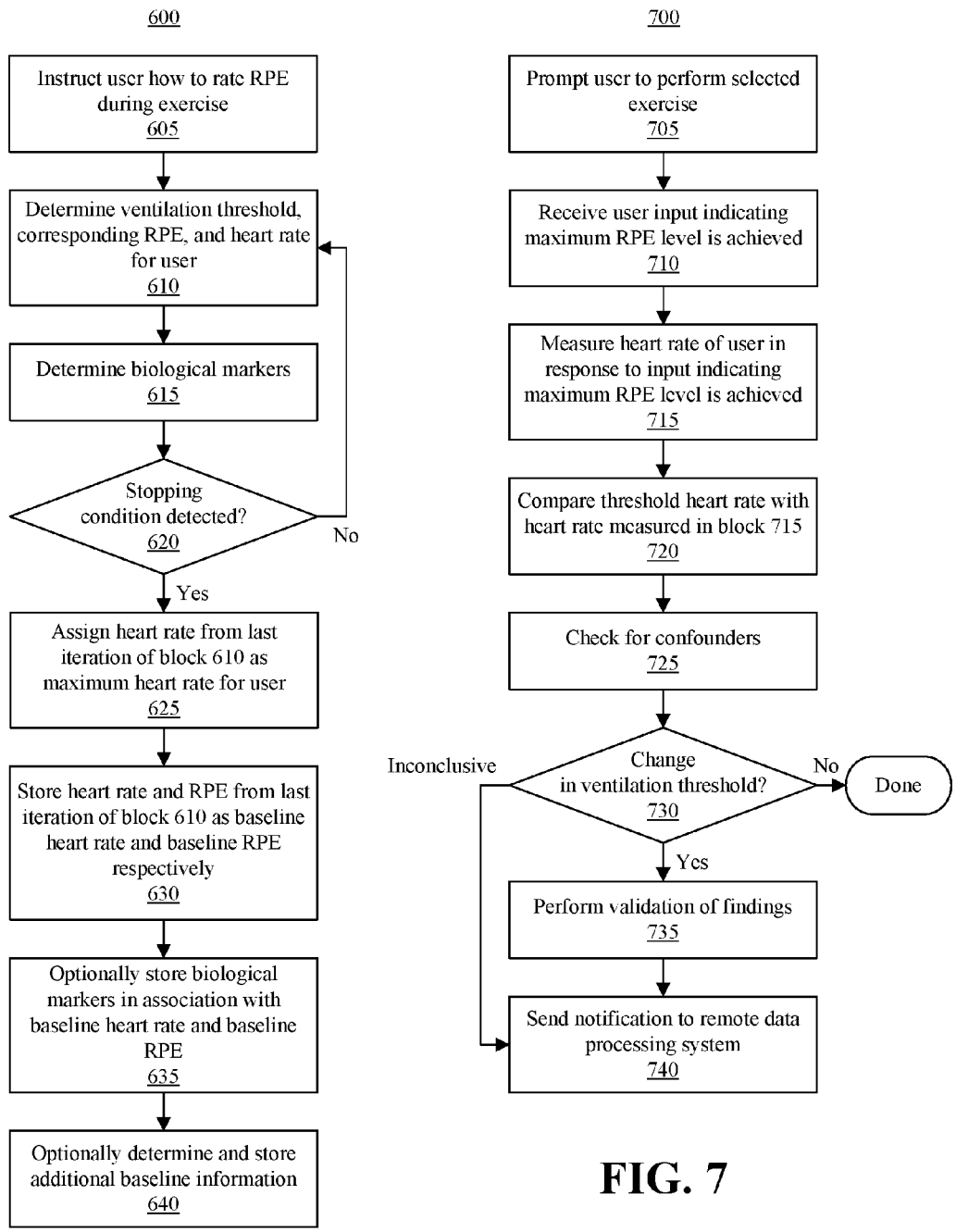
FIG. 6 illustrates a method of implementing a calibration phase for collecting data.
FIG. 7 illustrates a method of detecting ventilation threshold and/or a change in ventilation threshold.

FIG. 6 illustrates a method 600 of implementing a calibration phase for collecting data for a patient. In an embodiment, the data that is collected may be used in detecting ventilation threshold and/or a change in ventilation threshold for a patient. In one or more embodiments, method 600 is implemented using a system having an architecture the same as or similar to the architecture described in connection with FIG. 1. In one or more embodiments, method 600 is implemented using another system such as a cardiopulmonary testing system, where the resulting data is stored and made available to a system as described in connection with FIG. 1.

In block 605, the patient is instructed how to rate or estimate a rating of RPE. In one example, the patient is instructed as to how to rate RPE using the Borg scale. For example, trained medical personnel may provide instruction to the patient while the patient is at a hospital or another medical facility. In another example, trained medical personnel may provide instruction to the patient through a communication channel such as via a telephone call, a video call, or the like while the patient is monitored remotely. The patient, for example, may be monitored using tele-monitoring or another remote monitoring technology including an Internet or Web-based monitoring technology.

In block 610, the ventilation threshold, the corresponding RPE, and the corresponding heart rate for the patient are determined. For example, the patient may be outfitted with one or more sensors including a heart rate sensor. The sensor may be coupled to a system such as a cardiopulmonary testing system that is capable of directly determining ventilation threshold for the patient using available sensor(s). When the patient reaches, or approximately reaches, ventilation threshold, the system is capable of measuring the heart rate of the patient at that time. In addition, the system is capable of receiving an input from the patient specifying an estimated RPE value. The system is capable of storing the heart rate of the patient and the estimated RPE of the patient, where each corresponds to ventilation threshold of the patient.

In block 615, the system optionally determines one or more biological markers in response to the patient reaching ventilation threshold. In one or more embodiments, the system is capable of storing respiratory sound, e.g., a respiratory waveform, of the patient in response to the patient reaching ventilation threshold. The respiratory sound may be obtained using a sensor such as a microphone or a respiratory sensor. The respiratory sound may be stored with, or in association with, the heart rate and RPE corresponding to ventilation threshold for the patient. In an aspect, the respiratory sound of the patient upon reaching ventilation threshold may be stored and used as a biological marker.

In one or more embodiments, the system is capable of storing a measure of total energy expended in response to the patient reaching ventilation threshold. The total energy may be determined using an accelerometer where the total amount of energy expended by the patient may be measured as the output wattage from the accelerometer for the time period over which the patient exercises to reach ventilation threshold. The total energy expended by the patient upon reaching ventilation threshold may be stored and used as a baseline biological marker.

In block 620, the system is capable of determining whether a stopping condition is reached. If so, method 600 may continue to block 625. If not, method 600 may loop back to block 610 to continue. The determination of the ventilation threshold, the heart rate, and the estimated RPE for the patient may be repeated until the stopping condition is reached. In the case where biological markers such as respiratory sound and/or total energy expended are recorded, these biological markers may be determined also for each iteration of block 610.

For example, the system is capable of prompting the patient to perform an exercise without the patient being informed that the patient is about to reach ventilation threshold. In response to detecting that the patient is approximately at the ventilation threshold, the system can prompt the patient to obtain an estimate of the RPE value specified on the Borg scale. Further, the system is capable of again measuring the heart rate of the patient from sensor data at that time and/or the biological markers noted above.

An example of a stopping condition is where the patient is able to correctly and consistently assess the estimated RPE value of the patient's ventilation threshold. For instance, a stopping condition is satisfied when the difference between a predetermined number of consecutive estimated RPE values is below a threshold value. In another example, a stopping condition is satisfied when the mean square error of a predetermined number of estimated RPE values is less than a threshold value.

In block 625, the system is capable of assigning the heart rate determined in the last iteration of block 610 as the maximum heart rate for the patient. Further, the system is capable of setting the target heart rate for the exercise to the maximum heart rate and/or a percentage thereof.

In block 630, the system is capable of storing the heart rate from the last iteration of block 610 as the baseline heart rate or an average of the last N heart rate measurements found to meet the stopping condition as the baseline heart rate (where N is an integer value corresponding to the predetermined number of consecutive estimated RPE values above). The system is also capable of storing the RPE from the last iteration of block 610 as the baseline RPE or an average of the last N RPE values. The baseline heart rate and the baseline RPE are for, or correspond to, ventilation threshold of the patient, e.g., as opposed to being for the patient at rest or another context.

In block 635, the system optionally stores the biological marker(s) determined in block 615. In one aspect, the system is capable of storing the biological markers determined in the last iteration of block 615 for ventilation threshold or an average of the last N iterations of block 615 for one or both of the biological markers.

In block 640, the system optionally determines and stores data relating to the context of the patient. The data may be used to determine or detect the presence of confounders at a later time. Examples of data that may be stored include, but are not limited to, activity level, homeostatic disturbances, cardiac pathology, pulmonary pathology, musculoskeletal issues, environment, altitude, weather, and hydration.

For example, environment data such as particulate pollution level for the location of the patient during testing may be determined and stored with the ventilation threshold of the patient as part of the baseline data. The altitude and weather for the location of the patient during testing may be determined and stored with the ventilation threshold as additional baseline data. Other examples of baseline data may be collected over time and reflect the general health and/or state of the patient as opposed to the state of the patient while exercising. For example, activity level, homeostatic disturbances, cardiac pathology, pulmonary pathology, musculoskeletal issues may be determined during normal or resting circumstances and stored as baseline data for the patient.

In one or more embodiments, the system is capable of storing heart rate recovery data for the patient as additional baseline data. For example, the heart rate recovery of the patient, e.g., the change in heart rate for the patient post exertion or after reaching ventilation threshold, may be recorded and used as a baseline for later comparison. In one or more embodiments, heart rate recovery is used by the system as a validation mechanism for ensuring that ventilation threshold has occurred and/or has changed.

FIG. 7 illustrates a method 700 of detecting ventilation threshold and/or a change (e.g., a deterioration) in ventilation threshold for a patient. FIG. 7 illustrates a real time method of detecting ventilation threshold or a change in ventilation threshold for a patient that utilizes data as described and collected with reference to FIG. 6. In an embodiment, method 700 is performed by a system having an architecture the same as or similar to the architecture described in connection with FIG. 1.

In block 705, the system prompts the patient to perform a selected exercise. For example, the system may play an audio prompt or display a message using a patient interface prompting the patient to begin exercising. In addition, the system is capable of instructing the patient to perform the exercise and to provide an indication when the patient believes that the maximum RPE level is achieved. For example, during exercise at home, at a gym, in an unsupervised setting, etc., the system is capable of prompting the patient to initiate an exercise and to achieve a maximum RPE level for the exercise.

With the patient starting to exercise, the system is capable of monitoring the patient using one or more of the sensors described herein. For example, the system is capable of performing health monitoring as the patient exercises. The system is capable of monitoring the patient's heart rate using the heart rate sensor to generate a time series of sensor data. The system is also capable of monitoring other physiological and/or health indicators while the patient exercises.

In block 710, the system receives a patient input indicating that the maximum RPE level for the patient is reached. In an embodiment, the system is capable of providing a patient interface through which input(s) may be received from the patient. The input is indicative of the patient achieving the patient's maximum RPE level. The input may specify a particular RPE value.

In block 715, in response to receiving a patient input indicating that the maximum RPE level is achieved for the patient, the system measures the heart rate, or determines the heart rate of the patient from current sensor data. The system is capable of measuring the patient's heart rate and/or other physiological indicators in real time.

In block 720, the system is capable of comparing the previously stored baseline heart rate of the patient with the heart rate measured in block 715, e.g., when the patient indicated that the maximum RPE level was achieved. The system compares the current heart rate to the baseline heart rate, which is the heart rate for the patient at ventilation threshold.

In block 725, the system is capable of checking for one or more confounders. Examples of confounders include, but are not limited to, any of a variety of behaviors, medical conditions, or other data items that define a context for the individual. In one aspect, confounders are classified as either physiological or external. Examples of physiological confounders include activity level, homeostatic disturbances, cardiac pathology, pulmonary pathology, and musculoskeletal issues. Examples of external confounders include one's environment, altitude, weather, and hydration. Confounders and the detection of confounders are generally described following the discussion of FIG. 7.

In block 730, the system is capable of determining whether a change in the ventilation threshold for the patient is detected. For example, the system is capable of determining whether a deterioration in ventilation threshold for the patient is detected. The system is capable of detecting a change in ventilation threshold for the patient based upon the comparison performed in block 720. For example, the system is capable of determining whether the heart rate measured in block 715, e.g., the current heart rate, is higher, lower, or the same as the baseline heart rate.

If, for example, the current heart rate for the patient, as determined during exercise, is lower than the baseline heart rate corresponding to ventilation threshold for the patient, the system determines that the ventilation threshold has changed and, in particular, has decreased (improved). In one or more embodiments, the system is capable of replacing the baseline heart rate associated with ventilation threshold with the current heart rate for future comparisons.

If, for example, the current heart rate for the patient, as determined during exercise, is higher than the baseline heart rate corresponding to ventilation threshold for the patient, the system determines that the ventilation threshold has changed and, in particular, has increased (worsened). In one or more embodiments, the system is capable of replacing the baseline heart rate associated with ventilation threshold with the current heart rate for future comparisons.

If, for example, the current heart rate for the patient, as determined during exercise, is the same as the baseline heart rate corresponding to ventilation threshold for the patient, the system determines that the ventilation threshold has been reached and is unchanged. In one or more embodiments, the system is capable of maintaining the baseline heart rate associated with ventilation threshold for future comparisons.

In one or more embodiments, the system determines whether a change in ventilation threshold occurs based upon detecting an increase (decrease) above (below) a threshold amount. For example, the system is capable of determining that the user's heart rate increased or decreased as the case may be only when the difference from the baseline heart rate at ventilation threshold differs by more than the threshold amount.

Accordingly, if the system detects no change in ventilation threshold, method 700 can end. If the system detects a change in ventilation threshold, method 700 can continue to block 735. If the system determines that the change in ventilation threshold is inconclusive, method 700 can proceed to block 740. For example, if the system detects one or more confounders, the system determines that the ventilation threshold determination, whether increased, decreased, or the same, is inconclusive. More particularly, when the system detects one or more confounders in combination with reduced or increased heart rate, the system is unable to attribute the change in heart rate to a change in ventilation threshold.

In block 735, the system is capable of performing validation. The system is capable of validating a determination that a change in ventilation threshold has occurred for the user. In one aspect, the system is capable of using Respiratory Sinus Arrhythmia (RSA) for purposes of validating a determination that the ventilation threshold has changed. In the case where the system detects a rising heart rate, to remove the confounder effect, the system is capable of checking the magnitude of RSA during inspiration/expiration during exercise. This is because the heart rate naturally increases during the inspiration period, and decreases during the expiration period. Thus, it is important to compare only the corresponding phases in the baseline data and the test data. For example, as compared to the heart rate in the baseline time series of the heart rate data, if for the same effort level in the time series of heart rate test data, and same phase in RSA cycle (inspiration or expiration), the RPE for ventilation threshold (e.g., RPE=14) corresponds to a significantly higher or lower heart rate, then that is an indication that the ventilation threshold may have changed. In response to the system detecting this condition consistently over several sessions, the system determines that the ventilation threshold has changed. A lowering of the heart rate indicates improvement in ventilation threshold and increase in heart rate indicates worsening of the ventilation threshold.

In another aspect, the system is capable of using heart rate recovery for purposes of validating a determination that the ventilation threshold has changed. For example, in the case of detecting an increase in heart rate, the new RPE to heart rate relationship and the implication of a heart rate increase can be validated during the heart rate recovery component part of the heart rate time series of sensor data. If, for example, the higher heart rate is achieved by the user getting deep into the anaerobic threshold, the user will have a relatively (relative to the baseline case) activated sympathetic nervous system (SNS) during heart rate recovery. This phenomenon can be detected as a relatively reduced heart rate variability as compared to the baseline heart rate variability that may be stored as part of the baseline data for the user.

Regarding heart rate recovery, for example, the system is capable of determining whether the heart rate recovery is bi-exponential from the heart rate sensor data. A person's heart rate recovers from a maximum heart rate during exercise to a heart rate at rest at a rate of $e^{-kt}$. The system is capable of continuing to monitor heart rate for the user during recovery from exercise. The system is capable of fitting a curve to the heart rate recovery data for the user. A person of lesser health tends to have a more linear heart rate recovery. The system is capable of fitting a curve to the time series of heart rate data for the user to determine a value of "k." In one or more embodiments, the system is capable of validating an increase or improvement in fitness by detecting an increase in the value of k compared to a baseline heart rate recovery for the user. Conversely, the system is capable of validating a decrease or reduction in fitness by detecting a decrease in the value of k compared to a baseline heart rate recovery for the user. Determination of increase or decrease in fitness can act as a check to validate any ventilation threshold determination.

In block 740, the system is capable of sending a notification to a remote data processing system. The remote data processing system may be for a medical provider for the user. In one aspect, the system is capable of sending a notification that the ventilation threshold has changed. The notification may include the newly determined ventilation threshold. In one or more embodiments, the ventilation threshold may be specified in watts of power required for the user to reach ventilation threshold. In another aspect, the notification can specify or include sensor data, e.g., current sensor data such as heart rate. In another aspect, in the case where the determination of whether a change in ventilation threshold has occurred is inconclusive, the notification can specify any confounders that were detected within the sensor data.

In one or more embodiments, the notification can specify the corresponding health-related changes and causalities. Examples of such information provided to the remote data processing system can include sensor data or patient inputs indicating lack of exercise compliance, changes in medication or lack of medication regimen adherence, tobacco consumption, higher fluid consumption, progressive decrease in sleep, increase in depression, etc. This information can facilitate assessing the potential causality of the degradation in health.

In one or more embodiments, the system is capable of replacing the target heart rate if the RPE level reached during this exercise is lower than the RPE level determined as described in connection with FIG. 6. The replacement of the target heart rate, however, may be omitted.

As discussed, confounders relating to the detection of ventilation threshold and/or a change thereto may be physiological and/or external. The detection of a confounder while attempting to detect a change in ventilation threshold renders the detection inconclusive. The inventive arrangements described herein therefore are able to utilize wearable sensors to implement a conservative methodology for detecting changes in ventilation threshold that avoids providing notifications and/or warnings of worsening ventilation threshold in cases where confounders are detected.

Examples of physiological confounders include, but are not limited to, activity level, homeostatic disturbances, cardiac pathology, pulmonary pathology, and musculoskeletal issues. In one or more embodiments, the system is capable of detecting the presence of physiological confounders from the sensor data. The system is capable of ascertaining whether such confounders exist. In an aspect, the system is capable of determining that a confounder exists where a confounder is detected that was not detected within historical data. In another aspect, the system is capable of determining that a confounder exists where a confounder that did exist within the baseline data is found to deviate (e.g., deteriorate) compared to baseline and/or historical data.

Detecting lower or higher activity levels for the user immediately prior to the start of the ventilation threshold analysis are considered confounders. Regarding activity level, for example, the system is capable of monitoring activity level of the user from accelerometer data. The system may determine activity level based upon the power, e.g., wattage, generated by an accelerometer over time. Power output of the accelerometer may be used in place of estimates of the number of steps taken by the user. The system is capable of evaluating the user's walking or running speed, for example. In another example, the system is capable of detecting that the user has been climbing stairs in the recent past, e.g., prior to exercising.

The overall activity level may be compared with an activity level established for the user in the baseline data. In one or more embodiments, the system is capable of monitoring overall activity of the user for periods of time during which the user is not exercising. For example, the system is capable of detecting overall activity over extended periods of time and/or while the user is performing daily tasks. The system may detect a confounder in response to determining that the activity level of the user during a period immediately prior to the start of exercise is reduced compared to the baseline activity level for the user. As another example, the system may detect a confounder in response to determining that the activity level of the user during a period immediately prior to the start of exercise is increased compared to the baseline activity level for the user thereby indicating that the user is starting exercise already having performed a potentially strenuous activity and/or is more tired than usual.

Regarding homeostatic disturbances, for example, the system is capable of using sensor data to detect exposure of the user to stress, to detect sleep quality (e.g., sleep deprivation), etc. When under stress, for example, the user's Autonomic Nervous System (ANS) arousal and valence are typically in the second quadrant of the Circumplex Model of Emotions, which can be determined by heart rate and heart rate variability analysis where both trend down at the same time. In an embodiment, the system is capable of using heart rate and/or heart rate variability from the sensor data to determine whether the user is under stress and/or the amount of stress.

For example, the system is capable of determining whether the user is subject to stress and whether the amount of stress exceeds a baseline amount of stress based upon heart rate (e.g., energy) and heart rate variability (e.g., mood) of the user both being low (e.g., below a baseline for heart rate and/or a baseline for heart rate variability) at the same time and/or remaining low (concurrently) for at least a minimum amount of time. The baseline(s) may be specific to the user or generalized across one or more different users. Responsive to determining that the heart rate and heart rate variability both are low for at least the minimum amount of time immediately prior to exercise, for example, the system determines that the user is experiencing a higher than normal amount of stress, which the system considers a confounder.

In another example, the system is capable of detecting, from the sensor data, the confounder of sleep deprivation. For example, the system is capable of measuring sleep of the user using heart rate data and accelerometer data. The system is capable of determining the amount of time that the user sleeps and comparing the amount of time spent sleeping with a baseline amount of time (whether personal to the user or a generalized baseline determined across one or more other users) to determine sleep deprivation for the user. In one or more embodiments, the system is capable of monitoring sleep quality (e.g., sleep deprivation) for periods of time where the user is not exercising. For example, the system is capable of detecting sleep deprivation over extended periods of time including immediately prior to the start of exercise, which the system considers a confounder.

Regarding cardiac pathology, for example, the system is capable of detecting whether the user is chronotropically incompetent. The system is capable of detecting CI by monitoring sensor data and/or received patient inputs over a period of time. An example of detecting CI in a patient is described herein in connection with FIGS. 3, 4, and 5.

Regarding pulmonary pathology, for example, the system is capable of looking up user provided health history data to determine whether the user suffers from chronic obstructive pulmonary disease (COPD). COPD is a confounder for measuring ventilation threshold.

Regarding musculoskeletal issues, for example, the system is capable of using sensor data to determine whether the user suffers from joint problems. The system is capable of using accelerometer data to analyze the gait of the user. The system is capable of determining whether the user suffers from one or more joint problems based upon the gait analysis that is performed. The system is capable of determining that a musculoskeletal confounder exists in response to detecting a joint problem where such a joint problem did not exist within the baseline data. In another example, the system is capable of determining that a musculoskeletal confounder exists in response to detecting that a joint problem that existed in the baseline data has become worse. In one or more embodiments, the system is capable of monitoring for joint problems for periods of time during which the user is not exercising including the time immediately prior to the start of exercise. For example, the system is capable of detecting joint problems over extended periods of time and/or while the user is performing daily tasks.

Examples of external confounders include, but are not limited to, environment, weather, altitude, and hydration. In one or more embodiments, the system is capable of detecting the presence of external confounders from the sensor data, by querying one or more external data sources, and/or using user inputs that log user activities.

Regarding environment, for example, the system is capable of querying an external data source that lists environmental factors such as particle pollution (also referred to as particulate matter (PM)) based upon location. As used within this disclosure, the term "external data source" refers to an Internet-based or Web-based service or Website that may be queried for particular information. The system, for example, may include location data or obtain location data using GPS or another location determination technique, e.g., using WiFi networks, and query the external data source for the PM of the user's location during exercise. The system is capable of determining that the environment confounder is present or detected in response to determining that the current PM, or PM found while evaluating ventilation threshold, is different, e.g., higher, than the PM established in the baseline data.

Regarding weather, for example, the system is capable of querying an external data source, e.g., a weather service, to obtain information such as ambient temperature. If the ambient temperature for the location of the user is different from the ambient temperature where the baseline data is established, the system may consider the difference, e.g., a difference greater than a threshold amount, a confounder.

Regarding altitude, for example, the system is capable of querying an external data source based upon location to determine altitude. In another example, the system may be coupled to an altimeter so that the sensor data includes altimeter data. Oxygen saturation decreases at higher altitudes. If the altitude of the location of the user differs from the altitude where the baseline data is established, e.g., by more than a threshold amount, the difference may affect determinations relating to ventilation threshold and be considered a confounder.

Regarding hydration, the system may have access to user data specifying hydration information. As an illustrative example, the system or another device coupled to the system may execute a hydration tracking application. The user may enter data specifying hydration into the application. The system is capable of determining whether the user is sufficiently hydrated based upon a comparison of the user's hydration data to a baseline hydration level for the user. The system, for example, is capable of detecting the hydration confounder in response to determining that the user's hydration level is below the baseline hydration level during the time immediately prior to the start of exercise.

Figure 8:
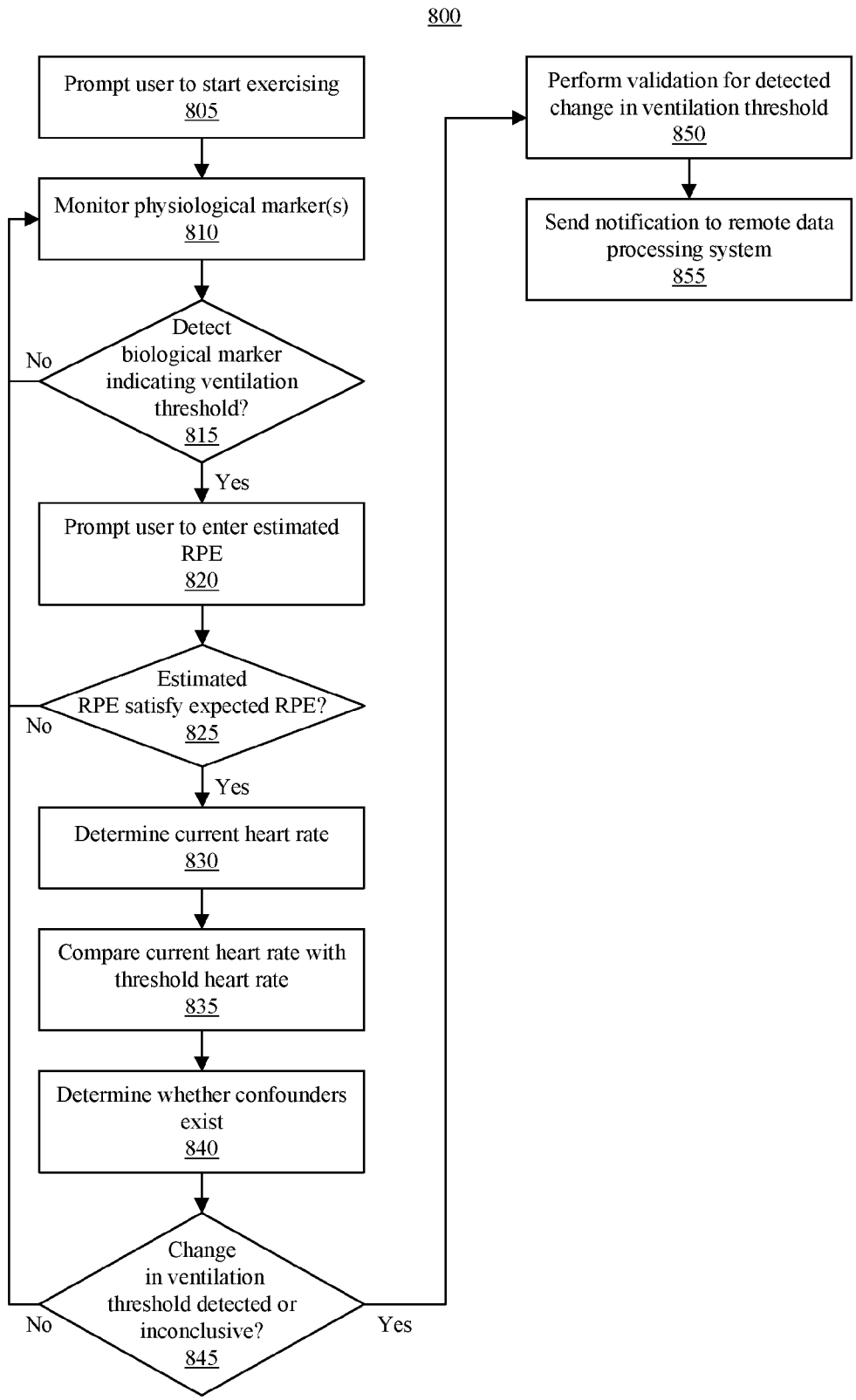
FIG. 8 illustrates another method of detecting ventilation threshold and/or a change in ventilation threshold.

FIG. 8 illustrates another method 800 of detecting ventilation threshold and/or a change in ventilation threshold for a patient. FIG. 8 illustrates a real time method of detecting ventilation threshold or a change in ventilation threshold for a patient that utilizes the baseline data described in connection with FIG. 6. In an embodiment, method 800 is performed by a system having an architecture the same as or similar to the architecture of FIG. 1.

In block 805, the system is capable of prompting the patient to begin exercising. In block 810, the system is capable of monitoring for one or more biological markers. In one example, the system is capable of monitoring the respiratory sound of the user. For example, the system may store a baseline respiratory sound of the user when in ventilation threshold. The system is capable of monitoring the respiratory sound of the user using a microphone or other respiratory sensor. Thus, the system monitors the real time sensor data by comparing the real time respiratory sound of the user to the baseline respiratory sound corresponding to ventilation threshold to determine a match.

In another example, the system is capable of monitoring the total activity of the patient. The system, for example, is capable of monitoring the power generated by an accelerometer over time as the patient exercises. The system is capable of using the power generated by the accelerometer as a proxy or indication of total activity of the patient. The system is capable of comparing the cumulative output power of the accelerometer over the time period that the patient exercises with a baseline for total activity, e.g., baseline total power, previously recorded when the patient reached ventilation threshold.

In block 815, the system determines whether a biological marker indicating ventilation threshold is detected. In response to detecting a biological marker, method 800 continues to block 820. If the biological marker is not detected, method 800 loops back to block 810. For example, the system is capable of determining whether the current respiratory sound of the patient matches the baseline respiratory sound thereby indicating that the patient has reached ventilation threshold. In another example, the system is capable of determining whether the total activity of the patient matches the baseline total activity thereby indicating that the patient has reached ventilation threshold. In still another example, the system is adapted detect both biological markers in order to continue to block 820.

In block 820, the system prompts the patient to enter an estimated RPE value. For example, the system is capable of generating a patient interface asking the patient to enter the estimated RPE. The patient interface may include a field or other patient interface element through which the patient may enter the estimated RPE. The system can receive a patient input specifying the estimated RPE.

In block 825, the system determines whether the estimated RPE entered in block 820 satisfies an expected RPE. For example, the system is capable of determining whether the estimated RPE is greater than or equal to a threshold RPE value such as 13. An RPE value of 13, for example, is indicative that the patient is at or is approaching ventilation threshold. If the estimated RPE satisfies the expected RPE (e.g., is at least 13), method 800 may continue to block 830. If the estimated RPE does not satisfy the expected RPE, e.g., the estimated RPE value is less than the threshold RPE value, method 800 may loop back to block 810 to continue monitoring as the system determines that the patient has not reached ventilation threshold.

In block 830, the system is capable of determining a current heart rate for the patient. The system is capable of determining the current heart rate for the patient from the heart rate sensor data that is being collected. The system determines the current heart rate for the patient in response to determining that ventilation threshold has been reached. In block 835, the system is capable of comparing the current heart rate with the baseline heart rate of the patient for ventilation threshold.

In block 840, the system determines whether one or more confounders exist. As discussed, the system is capable of detecting physiological confounders such as activity level, homeostatic disturbances, cardiac pathology, pulmonary pathology, musculoskeletal issues. The system is further capable of detecting external confounders such as environment, altitude, weather, and hydration.

In block 845, the system determines whether a change in ventilation threshold of the patient has occurred. The system determines whether a change in ventilation threshold for the patient has occurred based upon any detected change in heart rate from the comparison in block 835 and the existence, if any, of confounders from block 840.

If, for example, the current heart rate is lower than the baseline heart rate for ventilation threshold of the patient without having detected any confounders, the system determines that a change in ventilation threshold has occurred. In particular, the system determines that the ventilation threshold of the patient has decreased. If, for example, the current heart rate is higher than the baseline heart rate for ventilation threshold of the patient without having detected any confounders, the system determines that a change in ventilation threshold has occurred. In particular, the system determines that ventilation threshold of the patient has increased. If, for example, the system detects one or more confounders, the system determines that any change in heart rate that is detected is not determinative of whether a change in ventilation threshold for the patient has occurred.

In response to determining that a change in ventilation threshold has occurred or that the result is inconclusive (e.g., due to one or more confounders), method 800 continues to block 850. In response to determining that no change in ventilation threshold has occurred, method 800 loops back to block 810 to continue processing.

In block 850, the system is capable of performing validation for a detected change in ventilation threshold. It should be appreciated that block 850 may be omitted or skipped in the case where the result is indeterminate.

In one aspect, the system is adapted to perform validation by evaluating the heart rate recovery of the patient. As discussed, the system is capable of analyzing the heart rate recovery of the patient to ensure that the heart rate recovery follows a bi-exponential curve. In one or more embodiments, the heart rate recovery of the patient may be compared to prior heart rate recovery data, e.g., a baseline heart rate recovery for the patient. The system may validate an increase in ventilation threshold by determining that the value of k in the bi-exponential expression increases when curve fitting heart rate recovery data for the patient. The system may validate a decrease in ventilation threshold by determining that the value of k in the bi-exponential expression decreases when curve fitting heart rate recovery data for the patient.

In block 855, the system is capable of sending a notification to a remote data processing system. The remote data processing system may be a server of a medical services provider, hospital, doctor, or the like. Examples of notifications include, but are not limited to, a text message, a short message service (SMS) message, an electronic mail, etc. The notification may state that a change in ventilation threshold for the patient is detected. The notification may include additional data such as validation data, sensor data recently collected from the patient, etc.

In the case where the result is inconclusive, the system may send a notification stating that the result was inconclusive and include any additional data such as confounder(s) detected, sensor data, and the like. It should be appreciated that in one or more embodiments, the system is adapted to provide notifications specifying the foregoing types of data in cases where the system determines that ventilation threshold of the user has not changed in order to provide medical services providers with useful information relating to the user.

As discussed, another example of a biological condition that may be detected by the system is depression. Table 2 illustrates the PHQ-2. The PHQ-2 is often used for purposes of screening individuals for depression. The PHQ-2 includes two questions relating to the mood of the patient over the past two weeks. The answer given by the patient has a score of 0, 1, 2, or 3. The PHQ-2 is scored by summing the score for the two questions.

TABLE 2

| Over the past two weeks, how often have you been bothered by any of the following problems? | Not at all | Several days | More than half the days | Nearly every day |
|---|---|---|---|---|
| 1. Little interest or pleasure in doing things | 0 | 1 | 2 | 3 |
| 2. Feeling down, depressed, or hopeless | 0 | 1 | 2 | 3 |

Table 3 below illustrates the probability of a patient having a major depressive disorder or any depressive disorder based upon possible scores of 1, 2, 3, 4, 5, or 6.

TABLE 3

| PHQ-2 Score | Probability of Major Depressive Disorder (%) | Probability of any Depressive Disorder (%) |
|---|---|---|
| 1 | 15.4 | 36.9 |
| 2 | 21.1 | 48.3 |
| 3 | 38.4 | 75.0 |
| 4 | 45.5 | 81.2 |
| 5 | 56.4 | 84.6 |
| 6 | 78.6 | 92.9 |

The PHQ-2 does not have significant resolution for elucidating different aspects of depressive behavior. The PHQ-9 is considered more effective in this regard. Table 4 below illustrates the PHQ-9.

TABLE 4

| Over the past two weeks, how often have you been bothered by any of the following problems? | Not at all | Several days | More than half the days | Nearly every day |
|---|---|---|---|---|
| 1. Little interest or pleasure in doing things | 0 | 1 | 2 | 3 |
| 2. Feeling down, depressed, or hopeless | 0 | 1 | 2 | 3 |
| 3. Trouble falling or staying asleep, or sleeping too much | 0 | 1 | 2 | 3 |
| 4. Feeling tired or having little energy | 0 | 1 | 2 | 3 |
| 5. Poor appetite or overeating | 0 | 1 | 2 | 3 |
| 6. Feeling bad about yourself - or that you are a failure or have let yourself or your family down | 0 | 1 | 2 | 3 |
| 7. Trouble concentrating on things, such as reading the newspaper or watching television | 0 | 1 | 2 | 3 |
| 8. Moving or speaking so slowly that other people could have noticed. Or the opposite - being fidgety or restless that you have been moving around a lot more than usual | 0 | 1 | 2 | 3 |
| 9. Thoughts that you would be better off dead, or of hurting yourself in some way | 0 | 1 | 2 | 3 |

Table 5 below shows how the PHQ-9 is scored.

TABLE 5

| PHQ-9 Score | Depression Measure |
|---|---|
| 1-4 | Minimal depression |
| 5-9 | Mild depression |
| 10-14 | Moderate depression |
| 15-19 | Moderately severe depression |
| 20-27 | Severe depression |

A system using architecture 100 or an architecture similar thereto is capable of collecting data using the various sensors of the system or sensors coupled thereto. The system further is capable of analyzing the sensor data to identify or detect one or more markers for depression.

The baselines used for detection of markers of depression may be determined using any of a variety of different techniques. In one embodiment, the baselines may be generalized across a particular population of patients. For example, the baselines may have a resolution along an axis of gender, age, socioeconomic conditions, comorbidity, etc. In that case, such baselines are not specific to the patient of the system.

In another embodiment, one or more or all of the baselines used may be specific to the patient of the system. For example, such baselines may be determined by analyzing the sensor data of the patient during times that the patient is not experiencing a depressive mood. In a further embodiment, the determination of whether a marker is detected is based upon baselines adapted for evaluation on a daily basis. For example, the baseline may be one that is adjusted for evaluating sensor data for the current day as opposed to evaluating sensor data over a plurality, e.g., 14, days.

The system is capable of selectively administering one or more surveys based upon monitoring a patient for one or more of the markers of depression. Within this disclosure, the term "survey" is used interchangeably with the term "questionnaire." In one example, the survey is the PHQ-2 or a derivative thereof. In another example, the survey is the PHQ-9 or a derivative thereof.

The following describes various markers for depression and the detection of such markers. A system as described herein is capable of analyzing sensor data to detect the markers discussed. One example marker for depression is a low activity level of the patient. The system is capable of determining the activity level of the patient using sensor data generated by the accelerometer and/or the motion sensor. The system is capable of comparing the activity level of the patient with a baseline activity level. Responsive to determining that the activity level of the patient remains below the baseline activity level for at least a minimum amount of time, for example, the system detects the low activity level marker.

In one or more embodiments, the system is capable of classifying activities of the patient. The classification may be performed using known machine learning technologies. For example, the system is capable of classifying activities, e.g., daily chores requiring less, etc. compared to other more active activities such as exercise. The system is capable of detecting a lack of variety in the activities. For example, the system is capable of detecting that the patient performs bare minimum daily chores. The lack of variety in activities is another way of detecting the low activity marker indicating that the patient is engaged in a depressive pattern. In one or more other embodiments, the system is capable of using both activity level in combination with activity classification in detecting the low activity level marker.

Another example marker for depression is reduced amount of time spent outdoors (e.g., or too much time indoors). The system is capable of determining whether the patient is outdoors (or indoors) from location data generated by the GPS receiver. The system is capable of determining the amount of time that the patient is indoors and/or outdoors and comparing the amount of time outdoors with a baseline amount of time. Responsive to determining that the amount of time spent outdoors by the patient does not exceed the baseline amount of time, the system detects the marker of spending reduced time outdoors.

Another example marker for depression is being homebound. The system is capable of determining whether the patient is homebound (e.g., at home or at a particular location) using location data and comparing the amount of time spend at the designated location to a baseline amount of time. Responsive to determining that the amount of time spent at the designated location exceeds the baseline amount of time, the system detects the homebound marker.

Another example marker for depression is a low level of interaction with other people. Individuals that are depressed tend to spend less time interacting with others and the outside world. Such individuals tend to exhibit an introverted profile, which can significantly reduce the amount of emotional support the individuals may receive at the particular time that emotional support is most needed.

One form of interaction is speaking with other patients. In one embodiment, the system is capable of using audio data to determine an amount of time that the patient is interacting with other persons. The system is capable of sampling audio using the microphone from time-to-time throughout the day, periodically, or responsive to particular events. For example, the system is capable of sampling audio using the microphone when the patient may be engaging in a face to face conversation. The system is capable of analyzing the audio, e.g., performing voice analysis and/or voice recognition, to determine whether the patient is speaking and/or speaking with another person. Further, the system is capable of measuring the amount of time spent speaking based upon the analysis. The system further may approximate the amount of time spent speaking based upon the frequency at which samples are acquired and/or the number of samples acquired.

In another embodiment, the system is capable of analyzing call logs, which are considered part of the sensor data for purposes of this disclosure, to determine the amount of time the patient spent talking with others. The system is capable of determining the total amount of time using one or both of the techniques described. For example, the system may sum the time spent speaking as determined from the call logs and the sampled audio data.

In one or more other embodiments, the system is capable of determining the amount of time spent, e.g., via call logs, interacting with others through voluntary conversation with friends and/or family members. The party to which the patient is speaking and the party's relationship to the patient may be determined, for example, from a contact list stored within the system or a contact list that is accessible by the system. The system is capable of using the relationship of the other party on a call as an indicator of the patient's level of enthusiasm in interacting with the external world. Lack of enthusiasm is marker of well-known energy dynamics involved in personal interaction with the external world and an indicator of a melancholy mood.

The system is capable of comparing the amount of time spent interacting with other persons with a baseline amount of time for interacting with other persons. The system is further capable of determining a measure of enthusiasm and comparing the level of enthusiasm with an energy dynamics baseline. Responsive to determining that the amount of time spent interacting with other persons does not exceed the baseline amount of time for interacting with other persons and/or that the patient's level of enthusiasm is below the energy dynamics baseline, the system detects the low level of interaction marker. In one or more other embodiments, the patient's relationship to the other party on a call may be used as a quality factor, e.g., a multiplier, for the call time with that patient to weight calls with family or friends more heavily than other calls. Similarly, calls determined to be with persons other than family and/or friends, e.g., business calls and/or telemarketing calls, may be unweighted (have a quality factor of 1) or weighted using a quality factor less than one for purposes of comparison to a baseline. In this manner, calls may be valued differently for purposes of comparison with a baseline based upon the relationship of the party to whom the patient is talking.

In another embodiment, the system is capable of analyzing the tone and/or modulation of the patient's voice as a marker for depression. The tone and/or modulation of the patient's voice is an indicator of mood of the patient. The system, for example, is capable of detecting crying, supplicatory speech, apathic (disinterested) syndrome, length in time of pauses, (average) vocal pitch, mean loudness, and/or variation of loudness over time. Responsive to determining one or more of the characteristics of the patient's voice noted herein, the system detects a marker of depression. The marker for depression may be an independent marker for depression or a subset of the low level of interaction marker.

Another example marker for depression is decreased sleep. Patients with depression may be prone to insomnia or disturbed sleep which can be determined using one or more sensors. For example, the system is capable of measuring sleep of the patient using HR data and accelerometer data. The system is capable of determining the amount of time that the patient sleeps and comparing the amount of time spent sleeping with a baseline amount of time. Responsive to determining that the amount of time the patient sleeps does not exceed a baseline amount of time for sleep, the system detects the decreased sleep marker. Another sign of worsening psychophysiological resilience can be detected during sleep via the measurement of HR or blood pressure (BP) as during sleep a person often has a much lesser extent of dipping phenomenon (for HR or BP) as compared to healthy individuals.

Another example marker for depression is significant patient supine time. The system is capable of using accelerometer data to determine that the patient is supine and the amount of time that the patient is supine. The system is capable of comparing the amount of time that the patient is supine with a baseline supine time. Responsive to determining that the amount of time that the patient is supine exceeds the baseline supine time, the system detects the significant supine time marker.

Another example marker for depression is low ANS arousal. Depression can affect the ANS arousal profile of the patient. When under depression the patient's ANS arousal and valence are typically in the 3rd quadrant of the Circumplex Model of Emotions, which can be determined by various methods that can detect ANS arousal and valence such as HR and HRV analysis where both trend down at the same time. In one embodiment, the system is capable of using heart rate sensor data to determine HR and/or HRV. For example, the system is capable of determining whether the patient is subject to stress and whether the amount of stress exceeds a baseline amount of stress based upon HR (e.g., energy) and HRV (e.g., mood) of the patient both being low (e.g., below a baseline for HR and/or a baseline for HRV) at the same time and/or remaining low for at least a minimum amount of time.

Another example marker for depression is high stress especially while interacting with the outside world. In one embodiment, the system is capable of using heart rate sensor data to detect stress by determining HR and/or HRV. For example, the system is capable of determining whether the patient is subject to stress and whether the amount of stress exceeds a baseline amount of stress based upon HR (e.g., energy) and HRV (e.g., mood) of the patient; with the HR being high (above a certain baseline) and HRV being low (e.g., below a baseline) at the same time and remaining so for at least a minimum amount of time. In another embodiment, the HRV method used may be a sympathovagal balance based HRV method. In one or more other embodiments, the system is capable of performing HRV analysis with the external world by sound analysis. In these embodiments, generally the sound is generated from a live source (as in contrast to a sound coming from an electronic media). A patient suffering from depression typically has far more instances of stress arousal when interacting with the outside world. The system is capable of comparing the HRV of the patient with a baseline HRV given a same or like sound analysis. Responsive to determining that the HRV of the patient matches the baseline, the system detects the ANS arousal marker.

In another embodiment, one may use the GSR (galvanic skin response sensor) of the patient to detect the arousal level by itself or with the use of HR, and use the HRV to detect the valence. In general, any method that can detect that valence and/or arousal can be used to determine if the patient is located in the 3rd quadrant of Circumplex Model of Emotions. In cases where the patient has limited mobility or where there is a robust EEG method, an EEG based approach can also be used which can provide both valence and arousal. One such EEG sensor is the well-known EEG sensor provided by Emotiv of San Francisco, Calif.

In another embodiment, the system includes one or more sensors, e.g., bio-sensors, configured to determine an HRV profile of the patient and an amount of chronic stress episodes experienced by the patient, which may activate the LHPA axis. Activation of the LHPA axis may be detected by the one or more sensors.

Other example markers include emotional state, etc. In another embodiment, the system is capable of measuring emotional state using image data obtained from the camera and/or facial recognition sensors. The system is capable of analyzing particular features of the patient's facial expression within the image data using, for example, the Facial Action Coding Scale (FACS). The system is capable of detecting those facial features indicative of depressive mood (a depressive emotional state). The system, for example, is capable of comparing features found in images over time to determine the amount of time the patient spent in a particular mood. Responsive to detecting one or more such facial features and/or determining that the patient is in such a state or mood for at least a minimum amount of time, the system detects the emotional state marker.

As discussed, mood recall for a patient is often inaccurate. The current mood of the patient tends to color or obscure the patient's recollection of moods from prior days. In accordance with one or more embodiments described herein, the system is capable of providing questions of the type and/or variety included in the PHQ-2 and/or PHQ-9. The questions may be modified to avoid reference to the past two weeks. For example, the questions may be reformulated to inquire whether the patient is currently feeling a particular mood instead of whether the patient has experienced such a mood in the past two weeks and how often.

Figures 9, 10:
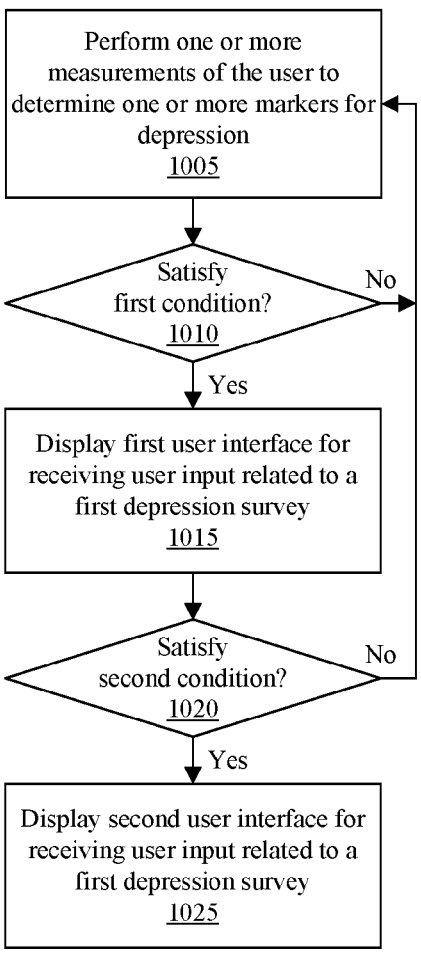
FIG. 9 is an example patient interface for presenting a survey.
FIG. 10 is an example method of sensor assisted depression detection.

FIG. 9 is an example patient interface 900 for presenting a survey. The survey provided in patient interface 900 is adapted from the PHQ-2 of Table 2. As pictured, rather than asking the patient about mood over the past two weeks, the questions presented ask the patient about his or her mood at the present time. As such, rather than selecting from one of four different answers that are weighted differently, the patient is provided with the binary choice of either "Yes" or "No" in answer to each question.

In one embodiment, the system, responsive to detecting one or more markers for depression, is capable of presenting PHQ-2 type question(s) without reference to the past two weeks. Such a question-set can be regarded as one member of a two week set (e.g., having 14 such instances). Responses of the patient may be stored in a database or other data structure which has the above information categorized so that a long term picture can be obtained by linearly adding the responses of the previous 14 days.

At any given time, e.g., during rehabilitation, the system is capable of determining whether the previous 14-days of response(s), e.g., the survey data, exceed a threshold score. In one example, the threshold score may be set to 2 for high sensitivity. In another example, the threshold score may be set to 4 for high specificity. In another embodiment, the threshold score may be determined based upon the available resources and the criticalness of the patient's condition. For low resource or relatively less extreme conditions, higher specificity can be targeted. In a setting with relatively abundant monitoring resources or more critical health conditions, a higher sensitivity can be targeted.

In one embodiment, if the score of the patient exceeds the threshold score, the system is capable of presenting the PHQ-9 and/or a derivative thereof. Further analysis of the patient's state of mind may be performed based upon the PHQ-9. The PHQ-9 can also be administered in the above manner where only a daily "slice" of the PHQ-9 is presented to the patient. The information over two weeks is updated and evaluated as is the case for the PHQ-2. In still another embodiment, if the score exceeds a pre-determined threshold, the system may automatically refer the patient to a medical provider. In an alternative embodiment, the survey data may be flagged to a medical provider, so that additional investigation can be conducted as to the mental state of the patient as appropriate.

Because patients are often resistant to filling out surveys and, in particular, surveys directed to depression, the system is capable of automatically administering one or more surveys. The survey(s) may be administered over one or more days, e.g., within a given time interval. The system administers a survey responsive to determining that a condition is met based upon one or more of the detected markers.

FIG. 10 is an example method 1000 of sensor assisted depression detection. Method 1000 may be implemented by a system having an architecture the same as, or similar to, the architecture of FIG. 1 or as otherwise described within this disclosure. In one embodiment, the performance of method 1000 may be limited or restricted so that the first survey or the second survey is presented no more than one time per day. Further aspects and details are described below with reference to FIG. 10.

In block 1005, the system performs one or more measurements of the patient to determine one or more of the markers of depression. For example, the system utilizes the sensors to generate and/or collect sensor data. The system further is capable of analyzing the sensor data to detect or identify markers for depression. In identifying or detecting markers for depression, the system is capable of comparing sensor data that is collected with one or more baselines.

In block 1010, the system determines whether a first condition is satisfied. Satisfaction of the first condition triggers presentation of the first survey. In one embodiment, the first condition defines the number markers for depression that are to be detected before a first survey is presented to the patient. In one example, the system may satisfy the first condition by detecting one marker during a day. In another example, the system may satisfy the condition by detecting two or more different markers during the day. In any case, if the first condition is satisfied, method 1000 proceeds to block 1015. If the first condition is not satisfied, method 1000 can loop back to block 1005.

In block 1015, the system displays a first patient interface for receiving patient input related to a first depressive survey. For example, the system displays one or more questions of the variety of the PHQ-2. As noted, the questions may lack reference to the prior two weeks. For example, the system may present a patient interface as described in connection with FIG. 9. The system is capable of receiving survey data in the form of responses to the questions from the patient via the presented patient interface.

In block 1020, the system determines whether a second condition is satisfied. If so, method 1000 continues to block 1025. If not, method 1000 loops back to block 1005. In one embodiment, the system determines whether the score of the first survey exceeds a threshold score. The threshold score may be one that is indicative of depression in the patient.

In block 1025, the system displays a second patient interface for receiving patient input related to a second depressive survey. In one embodiment, the second survey is the PHQ-9 or a derivative thereof. For example, the questions presented by the second patient interface may lack reference to a prior time period as is the case with the first patient interface and the first survey.

Figure 11:
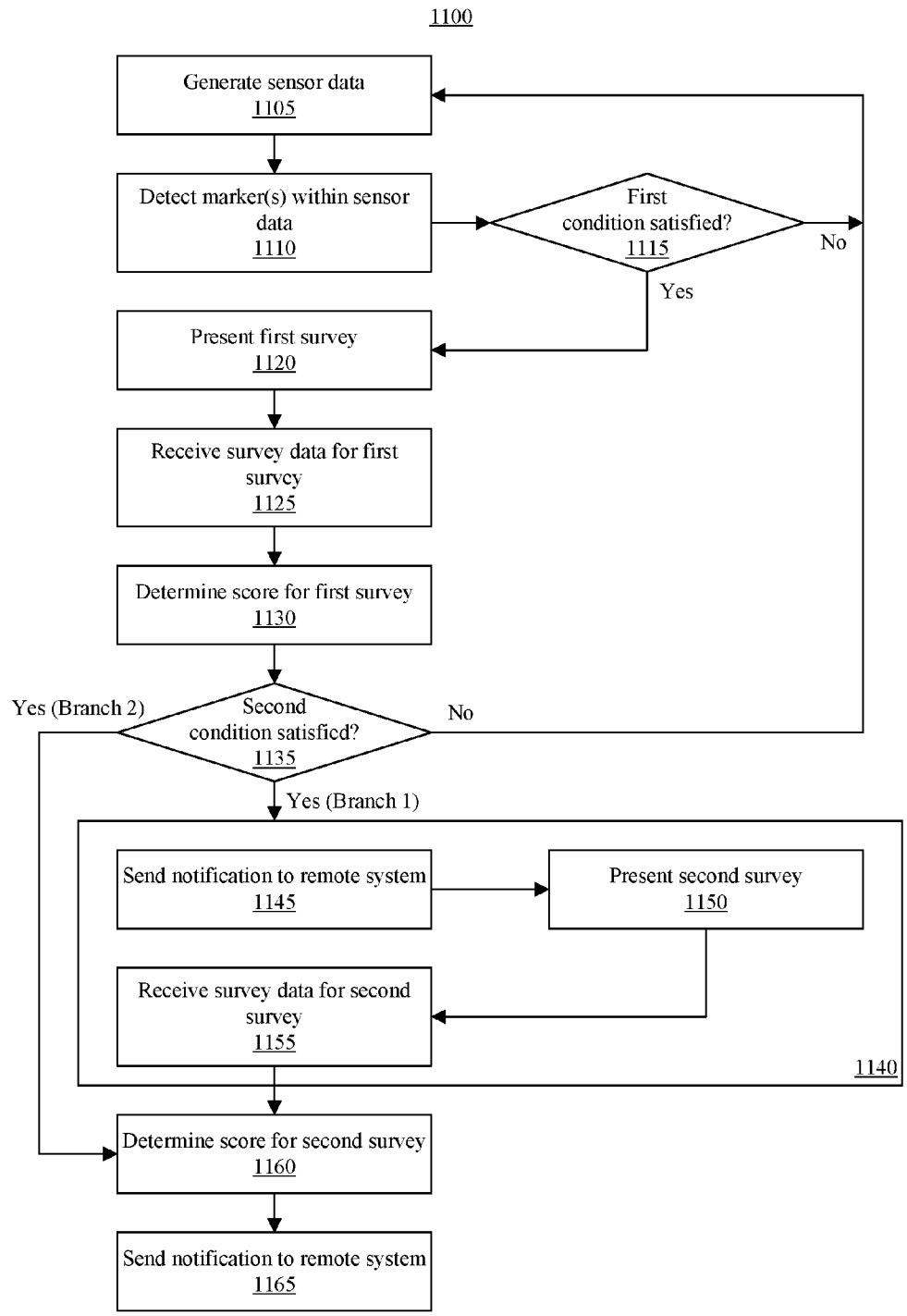
FIG. 11 is another example method of sensor assisted depression detection.

FIG. 11 is another example method 1100 of sensor assisted depression detection. Method 1100 may be implemented by a system having an architecture the same as, or similar to, the architecture of FIG. 1 or as otherwise described within this disclosure. In one embodiment, the performance of method 1100 may be limited or restricted so that the first survey or the second survey is presented no more than one time per day. Further aspects and details are described below with reference to FIG. 11.

In block 1105, the system generates sensor data. For example, one or more of the sensors of the system generate sensor data that may be stored in memory of the system as one or more data structures. Examples of sensor data include accelerometer data generated by the accelerometer; location data (e.g., GPS coordinates) generated by the location processor and/or motion sensor; proximity data generated by the proximity sensor; image data generated by the camera subsystem; audio data generated by the audio subsystem; heart rate data generated by the heart rate sensor, and so forth. The system is capable of generating and storing sensor data over a plurality of days.

In block 1110, the system is capable of detecting one or more markers within the sensor data. For example, the system is capable of analyzing the sensor data to determine whether one or more markers exist within the sensor data.

In block 1115, the system determines whether a first condition is satisfied. Satisfaction of the first condition triggers presentation of the first survey. In one embodiment, the first condition defines the number markers for depression that are to be detected before a first survey is presented to the patient. In one example, the system may satisfy the first condition by detecting one marker during a day. In another example, the system may satisfy the condition by detecting two or more different markers during the day. In any case, if the first condition is satisfied, method 1100 proceeds to block 1120. If the first condition is not satisfied, method 1100 can loop back to block 1105 to continue generating sensor data and monitoring for marker(s) for depression within the sensor data.

In block 1120, the system presents the first survey. The system is capable of presenting the questions of the survey through a patient interface of the system. In one embodiment, the system presents the PHQ-2 or an adaptation thereof. As noted, one adaptation is that questions are asked regarding how the patient currently feels as opposed to how the patient has felt over the past 14 days.

In one example, the system displays the questions of the survey through a visual patient interface. For example, the system is capable of displaying a patient interface as shown in FIG. 9. While FIG. 9 illustrates both questions being presented concurrently, in another embodiment, the system may present the questions one at a time in serial fashion. In another embodiment, the system may read the questions of the survey aloud to the patient. It should be appreciated that the particular modality used to provide the survey through the system is not intended as a limitation of the example embodiments described herein.

In block 1125, the system receives survey data for the first survey as specified by one or more received patient inputs. The patient interface of the system is configured to receive patient input providing answers to the questions referred to herein as survey data. The patient input may be touch patient input, keyboard patient input, speech, and so forth. The patient input specifying the survey data may be provided using any of a variety of different modalities.

In one embodiment, the system is configured to present the first survey no more than one time within a specific time period. For example, responsive to determining that the first condition is met, the system presents the first survey. The system does not provide the first survey to the patient again within the time period regardless of whether the first condition is again met during that same time period. In one example, the time period is a calendar day. In another example, the time period is 24 hours. In order to present the first survey again and obtain further survey data, the system first determines that a new time period has begun and that the first condition is satisfied in the new time period.

The system is further capable of storing received survey data for at least an amount of time necessary to determine a score for the first and/or second surveys. If, for example, the window of time considered for a particular survey is 14 days, the system is capable of storing survey data for at least 14 days. The system may store survey data longer than the required window of time and only utilize the survey data within the window of time when calculating scores for the first and/or second surveys. Appreciably, the system stores the survey data in association with a time and date stamp.

In block 1130, the system determines a score for the first survey. In one embodiment, the score is an estimated score. The system determines whether the patient provided an affirmative (e.g., a "Yes") answer to each question of the first survey from the survey data. Table 6 below illustrates how each question of the first survey is scored based upon whether the answer was "No" or "Yes." The score for each question is summed to determine a score for the first survey. Within Table 6, the value of N is the number of days that the particular question being scored in the first survey is answered affirmatively over a window of time "M."

TABLE 6

| Answer | Scoring |
|---|---|
| No | 0 |
| Yes ($1 \leq N \leq 7$) | $1 + (N - 1)/7$ |
| Yes ($8 \leq N \leq 12$) | $2 + (N - 8)/5$ |
| Yes ($13 \leq N \leq 14$) | 3 |

For purposes of illustration, consider the case where the patient is presented with question 1 and answers affirmatively, e.g., with a "Yes." Further, the patient has answered question 1 of survey 1 affirmatively one other time within the window of time. The time window is 14 days in this example. In that case, the value of N for question 1 is 2. The system calculates the score for question 1 of survey 1 using the expression $1+(N-1)/7$ with N=2 to obtain a score for question 1 of 0.286. The system is capable of storing survey data for the window of time. Thus, with the passing of each day, the window of time is a sliding window of time, e.g., a sliding 14-day window in this example.

The system scores the second question in the same way as question 1. It should be appreciated, however, that the value of N for a question is specific to that question and depends upon the number of times that particular question has been answered affirmatively over the window of time. Since the system scores question 2 using the same technique as question 1, but using a value of N that is specific to question 2, the particular expression used to determine a score for question 2 may differ from the expression used to calculate the score for question 1.

In further illustration, consider the case where the patient is presented with question 2 and answers affirmatively, e.g., with a "Yes." The patient has answered question 2 of survey 1 affirmatively 8 other times within the window of time. In that case, the value of N for question 2 is 9. The system calculates the score for question 2 of survey 1 using the expression $2+(N-8)/5$ with N=9 to obtain a score for question 2 of 0.6. Again, the system scores the second question using the same technique, where the value of N is determined independently for question 2. As such, in this example, the particular expression used to determine the score for question 2 is different from the expression used to calculate the score for question 1.

In further illustration, consider the case where the patient is presented with question 1 and answers affirmatively, e.g., with a "Yes." The patient has answered question 1 of survey 1 affirmatively 11 other times within the window of time. In that case, the value of N for question 1 is 12. The system calculates the score for question 1 of survey 1 to be 3. Again, the system scores question 2 using the same technique, where the value of N is determined independently for question 2.

In one embodiment, the window of time or "M" is set to the amount of time or number of days over which the patient mood is to be evaluated. For example, both the PHQ-2 and the PHQ-9, when given in a conventional manner, ask the patient to evaluate mood over the prior two-week period. The PHQ-2 and/or the PHQ-9 are given one time using a two week look-back period. In the case of FIG. 4, the first survey is given each day that the first condition is met. The score is calculated for that day using the sliding (or rolling) window of time where N is determined for each question independently for the window of time. The window of time is set to 14 days since the look back period for the PHQ-2 and the PHQ-9 is two weeks.

Accordingly, the scoring performed by the system as described with reference to block 1130 is adapted for the case where the patient answers the survey using binary answers of yes or no with the survey being administered each day that the first condition is met. The PHQ-2 ordinarily utilizes two questions where the patient selects one of four possible answers to each question. Each answer is carries a different score. Because the questions of the first survey are directed to how the patient is feeling at the time the survey is administered, the responses are binary and the scoring mechanism described above is used.

The expressions described with reference to Table 6 provide a higher bias for higher numbers for N. In another embodiment, a scaling factor nay be added. In still another embodiment, the expressions of Table 6 used may be non-linear for calculating a score for the questions.

In block 1135, the system determines whether a second condition is satisfied. If so, method 1100 continues down yes branch 1 or yes branch 2. If not, method 1100 loops back to block 1105 to continue collecting and analyzing sensor data. In one embodiment, the system determines whether the score of the first survey exceeds a threshold score. The threshold score may be one that is indicative of depression in the patient.

Yes branch 1 and yes branch 2 illustrate alternative implementations of method 1100. Continuing down yes branch 1, for example, the system may perform one or more optional operations illustrated within block 1140. In one embodiment, in block 1145, the system optionally sends a notification to a remote system. For example, the system may send a message to the system or device of a health care provider, a medical provider, a mental health professional, etc. The message may indicate the score of the first survey or include other data indicating a need for follow-up with the patient. The message may be an electronic mail, a text or instant message, an automated call, or another form of communication. The particular type of message that is sent is not intended as a limitation of the embodiments described herein.

In another embodiment, method 1100 may bypass block 1145 and proceed from block 1135 directly to block 1150. In block 1150, the system may present a second survey. The second survey may be the PHQ-9 or a derivative thereof. In one aspect, the system presents a subset of the questions of the second survey. Within PHQ-9, questions 1 and 2 are identical to questions 1 and 2 of the PHQ-2. Accordingly, since the first two questions of the PHQ-9 are the two questions already presented to the patient as the first survey, questions 1 and 2 of the second survey need not be presented.

For example, the system is capable of presenting one or more of questions 3, 4, 5, 6, 7, 8, and/or 9 of PHQ-9. In one embodiment, as noted, the questions are adapted to inquire about the current mood of the patient. In one or more other embodiments, the system is capable of estimating answers to a portion of the questions for the second survey based upon sensor data already collected. For example, the system is capable of estimating answers for questions 3, 4, 6, 7, 8, and/or 9 from the sensor data. In illustration, the system may estimate an answer to question 3 based upon accelerometer data and heart rate data or any other suitable sensor or bio-sensing system that is capable of detecting low-valence and low-arousal state of the patient's ANS. The system may estimate an answer to question 4 based upon accelerometer data and/or any data that indicates movement or motion of the patient. The system may estimate an answer to question 6 using HR and/or HRV. In one or more embodiments, the HRV method used may be a sympathovagal balance based HRV method. The system may estimate an answer for question 7 based upon activity level of the patient. The system may estimate an answer for question 8 based upon audio data, accelerometer data (activity), and/or other motion data such as speed of movement of the patient. The system may estimate an answer to question 9 using low valence and low ANS arousal (e.g., as may be indicated by HR and/or HRV).

In another embodiment, the system is capable of estimating answers to one or more of questions 3-9 while presenting at least one of questions 3-9 to the patient in order to solicit and obtain survey data for the presented question(s). The system is capable of presenting only one or more selected questions of the second survey for which sensor data is less accurate in estimating answers. In one example, the system is capable of presenting only question 5 to the patient to obtain survey data for the second survey. In other examples, the system is capable of presenting only questions 5 and 9, presenting only questions 5 and 6, presenting only questions 5, 6, and 9, and so forth.

In block 1155, the system receives survey data for each of the questions of the second survey that are presented.

In block 1160, the system determines a score for the second survey. As discussed, the system calculates the score based upon any received survey data for the second survey, the score of the first survey (which is the score of the first question and the second question summed), and/or the estimated answers to questions of the second survey as determined from the sensor data. For any questions of the second survey for which an answer is estimated, it should be appreciated that the system is capable of analyzing sensor data over the window of time, e.g., 14 days, to determine a value for N that is question specific and determine a score for the question using the expressions described with reference to Table 6 or derivatives thereof as described herein. Thus, the value of N may be determined for each question of the second survey independently based upon the number of days within the window of time that the markers indicating an affirmative answer to the question are detected. As noted, in some embodiments, in order to detect a marker, the system may need to detect certain characteristics for a minimum amount of time during a day or whatever time period is used as the evaluation period (e.g., 24 hours).

In the case where method 1100 proceeds along yes branch 2 from block 1135 directly to block 1160, the system is capable of estimating an answer for each of questions 3-9 of the second survey. In one embodiment, the system is capable of estimating an answer to question 5 based upon sensor data. In another embodiment, the system may omit question 5 and adjust the scoring for the second survey accordingly. In any case, the system is capable of determining a score, e.g., an estimated score, for the second survey using only the score of the first survey and the estimated answers to the questions of the second survey as determined from the sensor data.

In block 1165, the system optionally sends a notification to a remote system. For example, the system may send a message to the system or device of a health care provider, a medical provider, a mental health professional, etc. The message may indicate the score of the second survey or include other data indicating a need for follow-up with the patient. The message may be an electronic mail, a text or instant message, an automated call, or another form of communication. The particular type of message that is sent is not intended as a limitation of the embodiments described herein.

In one or more other embodiments, additional sensors may be incorporated to provide measurements that, if available, may be used with the scores. Care providers may be provided information about markers (e.g., for depression or psychological state in general) as computed by the system and/or such other sensors. For example, ECG, camera, and/or ultrasound are several such sensors to determine the RR-intervals and, hence determine if both HR and HRV trend downward (indicating that the emotion of the patient is in the 3rd quadrant of the well-known Circumplex Model of Emotions, which is where depression is located). In one embodiment, the magnitude of HRV and HR changes can be assigned a proportional weight based upon the physiological traits of the given person. For example, an elderly person who is taking beta blockers may not see much elevation in HR when under stress but will find the effect on HRV to remain significantly large. Such information can be programmed in the system by the physician who is aware of what marker of ANS is dampened due to medication or an existing pathology. This information can also be programmed using publicly and widely available databases of the FDA approved medicines and their side effect.

In one or more other embodiments, the system is capable of querying the patient to measure stress right before sleep and/or measuring the quality of sleep to obtain information about the sleep related portion of PHQ-9, e.g., question 3.

In one or more other embodiments, the system is capable of examining pattern(s) of activities of the patient. The system, for example, is capable of detecting a sudden decrease in number of active periods along with a decrease in total activity with concomitant changes in other sensor based markers. The system may use such information to answer vitality related portions of PHQ-9 such as question 4.

In one or more other embodiments, the system may obtain daily weight related measurements. The system is capable of estimating an answer to the portions of PHQ-9 relating to changes in appetite, e.g., question 5.

This disclosure uses the PHQ-2 and PHQ-9 as example depression screening tools. The examples presented herein, however, are not intended as limitations of the embodiments described. Other depression screening tools may be used in place of the PHQ-2 and/or PHQ-9. In one or more embodiments, a survey such as the Major Depression Inventory (MDI) may be used as a screening tool. In one or more other embodiments, a survey such as the Web-Based Depression and Anxiety Test (WB-DAT) may be used as a screening tool. In each case, the scoring mechanisms described within this disclosure may be used and/or adapted to such other screening tools. For example, responsive to automatically detecting one or more of the markers for depression described herein, the system is capable of providing one or more of the screening tools (e.g., surveys) to the patient.

While stress has been discussed herein in as a confounder, the various techniques described herein for detecting stress may be used to detect stress as an independent biological condition. As such, a system implemented as described herein is capable of detecting stress as an independent biological condition using any of the previously described techniques for detecting stress whether or not such techniques were discussed in terms of detecting stress as a confounder.

As discussed with reference to FIG. 2, the second stage of the process described is directed to image analysis in order to detect various conditions such as edema, pupil dilation, particular states of coloration in the patient, and emotional state.

Edema, for example, whether dependent or pitting, almost universally accompanies congestive heart failure and requires urgent medical attention. The image analysis described herein may be used to detect both the extent of edema and the locations of edema. This allows the system to determine whether the edema is dependent. The system is also capable of combining edema detection with activity detection. As such, the system is able to more accurately determine whether the edema is dependent. As an illustrative example, a person that has been lying supine for most of the day may have edema in the buttocks rather than in the person's feet.

As pumping efficiency of the heart is increasingly compromised, reduced blood flow leads to the patient's skin color becoming progressively pale, gray, or cyanotic. Using image processing, skin color may be accurately detected and used to indicate or determine pumping capacity of the patient's heart and any anomaly in the flow of blood to the patient's upper limbs.

Regarding pupil dilation, within worsening heart failure, the sympathetic system of the patient is routinely over active. This causes the release of catecholamines that influence the blood flow to the patient's eyes due to the effect of the catecholamines on alpha adrenergic receptors. This leads to dilated pupils in the patient. Image analysis is capable of detecting pupil dilation in the patient.

Regarding emotional state, the system is capable of performing image analysis to detect emotional state of the patient. For example, the system is capable of performing facial feature detection on image data from the patient to determine the emotional state of the patient.

FIG. 12 illustrates an example method 1200 of image analysis for pupil dilation. Method 1200 may be performed by a system using an architecture the same as, or similar to, the architecture described in connection with FIG. 1. In one aspect, method 1200 may be performed as part of the second stage described with reference to FIG. 2.

Method 1200 may begin in block 1205, where the system prompts the patient to capture image data. For example, based upon performing stage 1 analysis as described herein, the system determines that there is a likelihood that patient is under emotional pressure such as being stressed, fearful, or in pain. Accordingly, the system prompts the patient to capture image data.

In this example, the system prompts the patient to take one or more pictures of the patient's eyes using the camera subsystem of the system (e.g., the camera of the mobile phone or other device). The system is capable of prompting the patient to take an image of the patient's eye with relatively close proximity. In one example, the system prompts the patient to take the image at a distance of approximately 10-15 inches from the patient's eye.

In an aspect, the system is configured to provide a prompt or notification to indicate that the image is insufficient for purposes of analysis in a variety of different circumstances. In an example, the system is capable of performing image processing to determine whether the image is of the user's eye or whether the image includes only a portion of the user's eye. In response to determining that the image is not of the user's eye or that only a portion of the user's eye is in the image, the system is capable of providing a prompt. The prompt may indicate the findings of the analysis and request that the user retake the image. In another example, the system is capable performing image analysis to determine whether the image is of a minimum acceptable quality, e.g., having sufficient or a minimum amount of illumination. If not, the system may provide a prompt of the analysis findings and request that the user retake the image.

In an embodiment, the system is capable of detecting the approximate position of the patient's eye using eye detection image processing and provide one or more cues to the patient to help the patient position the camera of the system to capture an image with the necessary quality.

In block 1210, the system receives the image. In block 1215, the system is capable of processing the image using one or more computer vision technique(s). The system is capable of estimating the amount of dilation in the pupil of the patient.

For example, as part of block 1215, the system is capable of performing color correction. The system is further capable of performing iris isolation or iris segmentation following color correction. The system is able to perform pupil detection following iris detection. In one aspect, the system applies one or more contour or edge detection and shape estimation methods. The shape estimation methods allow the system to accurately detect the position and shape of iris and pupil of the patient within the image.

In block 1220, the system uses the extracted contours for both the iris and the pupil to estimate the amount of dilation the pupil has undergone in the patient. Thus, an example of a visual characteristic utilized during the second stage is amount of dilation of the pupil. In one aspect, the amount of dilation is computed as a dilation ratio. The system is capable of calculating the dilation ratio as Dilation Ratio (dr)=(pupil diameter)/(iris diameter).

In an embodiment, the system is capable of calculating a range of the estimated dilation ratio. The range can be used by the system in computing a health estimate to minimize false positives or false negatives. Use of a range for the estimated dilation ratio provides the system with the capability of interpreting the data to minimize false positives or minimize false negatives. For example, a range for dilation ratio may be used in cases where the image is of poor quality that has not been fixed or cannot be fixed.

In block 1225, the system compares the dilation ratio for the patient with a reference dilation ratio. In an aspect, the reference dilation ratio is obtained from a reference image. The reference image may be obtained from a database or stored locally on the system and illustrate a dilation ratio for a healthy patient. In an aspect, the reference dilation ratio may be an expected value or a range of expected values, e.g., as may be provided from a healthcare provider. In an aspect, the reference image may be of the patient in a known, or healthy, cardiac state and be used as a baseline illustrating a known dilation ratio. In another aspect, the system may store a reference dilation ratio used for purposes of comparison. Accordingly, the system is able to accurately estimate the amount of deviation between the patient dilation ratio or the range of patient dilation ratio and the reference dilation ratio or a range of reference dilation ratio, as the case may be.

In another aspect, the system is capable of analyzing overall shape of the patient's eye to estimate edema in the eye of the patient. For instance, the system is capable of determining, e.g., estimating, the size of the patient's eye using image processing techniques described herein.

In block 1230, the system is capable of storing an estimate of deviation of pupil dilation in the patient compared to a reference dilation ratio. In another aspect, the system is capable of estimating the amount of edema (in the eye) suffered by the patient based upon the size of the patient's eye. The system is capable of providing the estimate of the amount of edema based upon size of the patient's eye, the estimate of deviation of pupil dilation, and/or both.

FIG. 13 illustrates an example method 1300 of image analysis for skin color. Method 1300 may be performed by a system using an architecture the same as, or similar to, the architecture described in connection with FIG. 1. In one aspect, method 1300 may be performed as part of the second stage described with reference to FIG. 2. Method 1300 illustrates an example method for determining whether a patient suffers from cyanosis or skin discoloration (pale skin).

Method 1300 may begin in block 1305, where the system prompts the patient to capture image data. For example, based upon performing stage 1 analysis as described herein, the system determines that there is a likelihood that patient is under emotional pressure such as being stressed, fearful, or in pain. Accordingly, the system prompts the patient to capture image data.

In this example, the system prompts the patient to take one or more pictures and/or video of the one or more regions of the patient's skin believed, by the patient, to exhibit difference in skin coloration. In case of central cyanosis, these regions include the areas around core of the body, lip, and tongue. In case of peripheral cyanosis, these regions include fingers or extremities in the body. In an aspect, the system may prompt the patient to capture image data of one or more or all of these particular regions of the patient's body. As the image data is collected, the system labels or correlates the particular images and/or videos with the part or region of the body that the patient was instructed to capture.

In block 1310, the system receives the image data. In block 1315, the system is capable of processing the image using one or more computer vision technique(s). The system is capable of analyzing the image data for quality as previously described and prompting the user to retake the image data in the case where the image data is determined to be of insufficient quality for accurate analysis.

Continuing with block 1315, the system is capable of estimating the amount of variation in skin coloration illustrated in the images compared to reference skin coloration. In one aspect, the system accounts for skin type in the analysis. Thus, an example of a visual characteristic utilized during the second stage is skin coloration of the patient.

The system is capable of performing analysis by comparing coloration of selected parts of the patient's body to reference coloration data. In one aspect, the reference coloration data may be other parts of the patient's body that typically do not exhibit variation in coloration. For example, the system is capable of comparing coloration in parts of the patient's body that characteristically exhibit variation in coloration for central cyanosis and/or peripheral cyanosis with other parts of the patient's body that do not typically exhibit variation in coloration for central cyanosis and/or peripheral cyanosis as the case may be. In that case, the system directs the patient to take image data of parts of the patient's body expected to exhibit color variation and image data of parts of the patient's body not expected to exhibit color variation for purposes of comparison.

In another aspect the system is capable of performing analysis by comparing coloration of selected body parts of the patient's body to reference coloration data that is obtained from a reference database that may be compiled from other patients or the instant patient in a healthy or known state. The reference coloration data may be reference images and/or reference data extracted from such images. In either case the reference coloration data may be stored in the system for purposes of comparison. The reference coloration data may also be correlated with particular body parts so that the system compares coloration of image data for a given body part (e.g., a finger) with reference coloration data for the same body part.

In block 1320, the system determines a discoloration score coefficient. In one aspect, the system calculates the discoloration score coefficient by comparing the coloration of parts of the patient's body in the image data with the reference coloration data described. The discoloration score coefficient indicates a level of deviation of skin color (pale or cyanotic) of the patient from healthy skin color.

In block 1325, the system stores the discoloration score coefficient. As such, the discoloration score coefficient is another example of a visual characteristic that may be used during the second stage.

Figure 14:
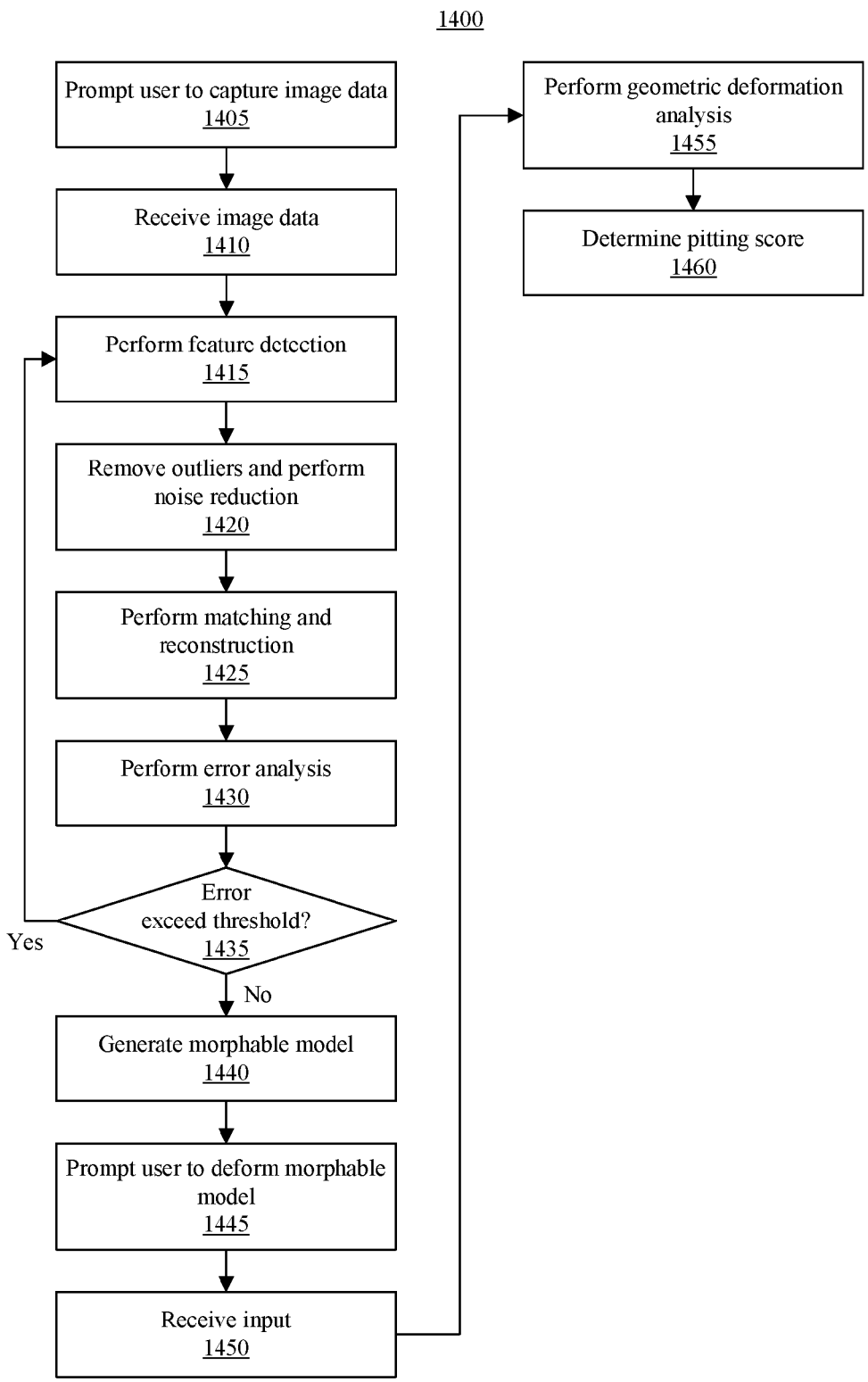
FIG. 14 illustrates an example method of image analysis for edema.

FIG. 14 illustrates an example method 1400 of image analysis for edema. Method 1400 may be performed by a system using an architecture the same as, or similar to, the architecture described in connection with FIG. 1. In one aspect, method 1400 may be performed as part of the second stage described with reference to FIG. 2.

FIG. 14 illustrates a general method where the patient is asked to capture image data of a body part of the patient or of the patient's body in general. The image data may be taken from multiple, different viewpoints. The system uses the image data to generate a three dimensional (3D) model of the body part of the patient. In one aspect, the 3D model is converted into a morphable model that allows the system to analyze an amount of pitting in the body part. The morphable model is manipulated through patient intervention (e.g., user inputs) or programmatically (e.g., automatically) to estimate the level of edema suffered by the patient.

Method 1400 may begin in block 1405, where the system prompts the patient to capture image data. For example, based upon performing stage 1 analysis as described herein, the system determines that there is a likelihood that the patient is under emotional pressure such as being stressed, fearful, or in pain. Accordingly, the system prompts the patient to capture image data.

The system prompts the patient to capture image data from multiple, different viewpoints. In one aspect, the system prompts the patient through a patient interface of the system. The prompt can provide instruction as to camera position of the system in relation to the patient. In case of error in image data capture, the system provides feedback to the patient to re-initiate the capture process.

In one or more embodiments, the system is capable of selecting a particular body part for which image data is to be collected. For example, in response to a determination that the patient has a low activity level or has spent a greater amount of time in a supine position (e.g., as compared to an expected amount of time or baseline amount of time spent in the supine position), the system may select the buttocks as a candidate body part for purposes of edema evaluation. The prompt provided from the system indicates the particular body part for which image data is to be collected. As noted, in cases where the patient is inactive, as determined from sensor data, the edema may be dependent. The system may determine that any edema detected is dependent based upon determining that the activity level of the patient is below a threshold and/or detecting that the patient has spent a minimum amount of time in a supine position prior to the edema analysis described herein.

In the case where the system determines that the patient is active and/or has not been in as a supine position as described above, the system selects a different body part such as fingers, arms, and/or legs for purposes of image data collection and edema evaluation.

In block 1410, the system receives the image data. The received image data may be labeled in accordance with the particular body part that the patient was asked to capture. For example, an image received in response to prompting the patient for an image of the patient's arm may be labeled "arm" in memory by the processor. Further, as noted, the system may instruct the patient, as part of the prompting, to capture more than one image of the selected part of the body from multiple, different viewpoints.

In response to receiving the image data, the system is capable of processing the image data using one or more computer vision technique(s). In one aspect, the image processing includes multiple stages. The system is capable of analyzing received image data for quality as previously described and prompting the user to retake the image data in the case where the image data is determined to be of insufficient quality for accurate analysis.

In block 1415, the system is capable of analyzing the image data using low level computer vision feature analysis. The system is capable of performing feature detection and extracting feature descriptors. Examples of feature that may be detected and/or extracted include, but are not limited to, scale-invariant feature transform (SIFT), histogram of oriented gradients (HOG), and so forth. In block 1420, the system is capable of removing outliers from the extracted features. Further, as part of block 1420, the system is capable of reducing noise in the extracted features.

In block 1425, the system performs matching and reconstruction. In one aspect, within block 1425, the system combines the image data, which includes images of the selected part(s) of the body of the patient under analysis for edema from multiple different viewpoints, into a 3D model of the part of the patient's body. Knowing the body part of the patient being modeled and the extracted features, the system is capable of generating the 3D model by combining the image data. It should be appreciated that if an insufficient amount of feature points are found, the system is capable of prompting the patient to take further images of the part of the patient's body under analysis.

In block 1430, the system is capable of performing an error analysis. In one aspect, the system performs a least squares error analysis process to estimate the error in the 3D model. Given a reference human body part, for example, the system is able to calculate a reconstruction error. In block 1435, the system determines whether the error exceeds a pre-determined error threshold. If the reconstruction error exceeds the pre-determined error threshold, the system is capable of re-initiating the reconstruction process. Accordingly, method 1400 loops back to block 1415 to continue processing. If the reconstruction error is at or below the pre-determined threshold, the system begins generation of a morphable model. Accordingly, method 1400 continues to block 1440.

In block 1440, the system generates a morphable model. In one aspect, the system converts the 3D model into a point cloud. The system is capable of rendering the morphable model using a pre-determined texture, a wireframe, etc. on the display of the patient's system.

In block 1445, the system prompts the patient to deform the morphable model in proportion to the deformation, or pitting, experienced by the patient on the body part under analysis. For example, the system displays the morphable model on the display of the system and prompts the patient to deform the morphable model to replicate the pitting experienced by the patient in the modeled body part. In block 1450, the system receives a patient input. The patient input (e.g., data), which may be a touch-based input to manipulate the displayed morphable model, deforms the morphable model a given amount. The patient-specified data indicates a deformation to the morphable model. The patient, for example, is capable of applying a stress input to the morphable model.

In block 1455, the system is capable of determining geometric characteristics for the deformed morphable model. For example, given the amount of deformation to the morphable model, the system is capable of performing a geometric analysis on the morphable model to calculate geometric characteristics of the deformation, e.g., pitting, such as width and/or length, circumference, depth, and so forth. If the computed geometric characteristics are more than established pre-determined threshold(s) for one or more of the determined geometric characteristics, the system determines that the patient is suffering from edema. It should be appreciated that the system is capable of computing more than one pitting deformation by examining more than one location on the user's body. The locations on the user's body examined by the system may be determined based upon input from the healthcare provider for the user or the user's evaluation of the regions where the user (e.g., the patient) feels to have a significant edema.

In block 1460, the system is capable of determining a pitting score (PScore) from the geometric characteristics that are generated. The PScore is an estimate of severity of edema suffered by the patient. The system may utilize any of a variety of pitting scores that correlate depth and/or time for the deformation to rebound with a severity of edema being experienced. In one aspect, the system is capable of sending the PScore to a medical service provider or a system of a medical service provider for further analysis.

In one or more embodiments, the system is capable of evaluating edema based upon how quickly the patient's skin recovers or "rebounds" from pitting. For example, the process described with reference to FIG. 14 may be performed for a first iteration to evaluate the size of pitting initially made. The patient may then be instructed to capture further image data periodically or at particular times, e.g., every 10-40 seconds.

In one aspect, the system is capable of performing image analysis to evaluate how quickly the pitting rebounds. Such analysis may be performed periodically based upon the collected image data (e.g., every 10-40 seconds) without having the patient apply a deformation to the morphable model. In another aspect, the system may present the non-deformed morphable model to the patient periodically. The patient may provide an input indicating the amount of pitting currently experienced by the patient to the morphable model. In either case, the system is capable of determining a rate of rebound for the pitting. In this regard, the system is able to calculate a rate of change in the pitting, e.g., a rebound rate, to better evaluate the severity of the edema.

As such, the geometric characteristics, the PScore, and/or the rebound rate are examples of visual characteristics that may be used during the second stage.

Figure 15:
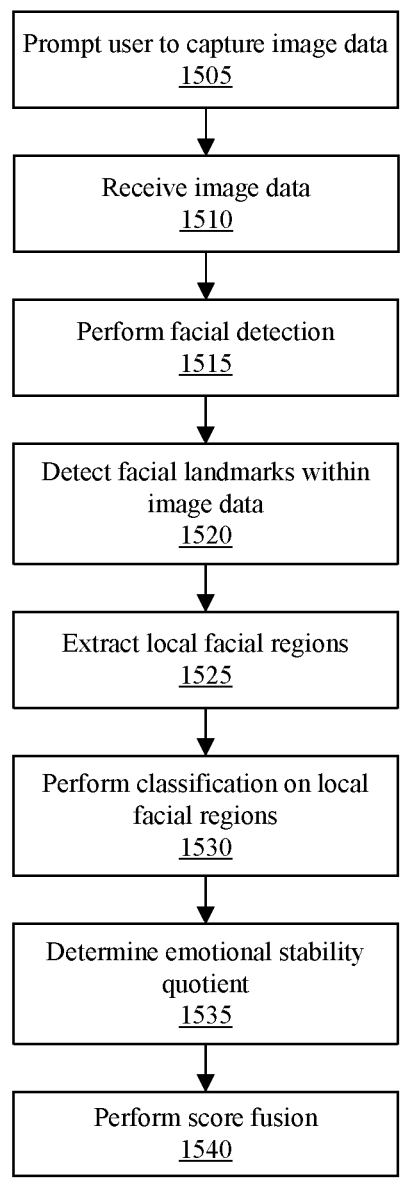
FIG. 15 illustrates an example method of image analysis for facial features.

FIG. 15 illustrates an example method 1500 of image analysis for facial features. Method 1500 may be performed by a system using an architecture the same as, or similar to, the architecture described in connection with FIG. 1. In one aspect, method 1500 may be performed as part of the second stage described with reference to FIG. 2. FIG. 15 illustrates an example process for analyzing and detecting a range of human emotions related to a patient's well-being.

Method 1500 may begin in block 1505, where the system prompts the patient to capture image data. For example, based upon performing stage 1 analysis as described herein, the system determines that there is a likelihood that patient is under emotional pressure such as being stressed, fearful, or in pain. Accordingly, the system prompts the patient to record a video of the patient's face for analysis. The system, for example, is capable of instructing the patient to turn on the front facing camera of the system or other device and hold the camera in front of the patient's face. The system instructs the patient to start recording.

In an aspect, the system is capable of providing the patient with feedback based on face detection data to finalize the camera position (e.g., to ensure the patient's face is within the image data). Once the camera position is finalized, the system is capable of analyzing the patient for signs of emotional pressure based upon image data obtained from the camera.

In block 1510, the system receives the image data. The system is capable of processing the image data using one or more computer vision technique(s). In one aspect, the system analyzes the image data through a facial feature detection pipeline. The system is capable of analyzing the image data for quality as previously described and prompting the user to retake the image data in the case where the image data is determined to be of insufficient quality for accurate analysis.

In block 1515, the system is capable of performing facial detection within the image data. The system identifies the face of the patient within the image data received in block 1510. In block 1520, the system is capable of detecting the locations of facial landmarks such as eyebrows, nose, lips, etc. from within the image data. In one embodiment, the system performs facial landmark detection using any of a variety of methods that may combine HOG descriptors and other low level vision features along with advanced machine learning and classification techniques. In block 1525, the system is capable of performing local facial region extraction using these facial landmarks. The system is capable of analyzing the local facial regions for intensity variations relating to the facial landmarks.

In block 1530, the system is capable of classifying the local facial regions. In one aspect, the system is capable of comparing the intensity of the local facial regions with stored predictive models.

In one embodiment, the predictive models may be created by analyzing facial regions of a wide range of patients under varying levels of emotional pressure. For example, predictive models may be built that predict human emotions such as pain, stress, and fear. Predictive models may also be built that predict human emotions such as happiness, excitement, calm, etc. In one aspect, the predictive models evaluate deformation of inter-face features and skin color variations.

For example, as part of generating the predictive models, data from local facial regions of a reference database of local facial regions from a large number of patients is grouped into data based upon the categories such as "patient under pain," "patient under stress," "patient under fear," etc. For each of these emotional states, data is grouped and labelled as belonging to a particular class. A discriminative multi-class classifier (e.g., an emotional state classifier) is built from extracted feature representations from the processed local facial regions of the patients in the reference database. In one aspect, discriminative classifiers such as support vector machines are trained on data from a wide range of patients with n-fold cross-validation. During the cross-validation stage, parameters are tuned to obtain optimal classification parameters. The trained predictive model can be stored in the system for use at a later time for providing predictions during operation.

Thus, during operation, e.g., during performance of method 1500, the predictive models are applied to determine the likelihood that the patient is experiencing stress, fear, and/or pain. In another embodiment, the system is also capable of using the patient's history in combination with the predictive models to determine likelihood that the patient is stressed, fearful, or in pain. For example, during operation, the system processes the face regions of the image data from the patient and extracts the local facial regions as described. The system is capable of transforming the local facial regions into feature vectors that are passed through the emotional state classifier.

In an embodiment, the system is capable of detecting states such as pain, stress, fear, and/or positive mood in conjunction with, or just by the use of, bio-sensors. The bio-sensors can involve use of any known approach that measures the psychophysiological state of the user using markers (e.g., as described herein) that reflect ANS arousal.

In block 1535, the system is capable of calculating an emotional stability quotient (ESQ) using the output from the predictive models and/or other meta-information obtained by the system as described herein. In one or more embodiments, the system is capable of using the predictive models, which may incorporate large scale machine learning and/or temporal filtering, to accurately track emotional pressure levels of patients over a given time frame.

In an embodiment, the system uses the raw decision scores (e.g., the distances from the classifier hyperplane) and uses the raw decision scores to determine a degree of each emotional state. As such, the system is able to model joint distribution of emotional state. The joint distribution of emotional state may become the basis of the decision system that is used to determine severity of emotional pressure. For example, ESQ can be used to provide feedback to estimate a level of intervention required by either a remote healthcare professional or emergency services. The ESQ may be used to help in triage when combined with existing data about ANS. Further, the ESQ when combined with ANS may be used to rule out false positives.

In block 1540, the system performs score fusion. In one aspect, the system, in executing the emotional state classifier, is capable of providing a prediction for each of the emotional states for which the emotional state classifier is trained. For example, the emotional state classifier may indicate that the patient is likely 20% fearful, 20% stressful, and 60% in pain. In one aspect, the system computes the prediction using the distance of the incoming feature vector to the hyperplane as the classification confidence of the classifier. In a further aspect, the system is capable of using majority voting to assign a prediction label (i.e., a prediction category to determine if the given image data contains a stressed/in pain or fearful individual).

As such, the classifications determined in block 1530, the ESQ, the predictions from the score fusion, and so forth are examples of visual characteristics that may be used during the second stage.

Having described the various biological conditions relating to the first stage and the image analysis performed as part of the second stage, the system is capable of determining whether cardiac failure in the patient is worsening as illustrated in block 230 of FIG. 2. It should be appreciated that the system may be tuned so that a determination that cardiac failure in the patient is worsening may be triggered based upon a determination that the patient suffers from an edema alone, a determination that the patient exhibits pupil dilation (e.g., deviation in pupil dilation from the reference) alone, a determination that the patient is under emotional pressure (experiencing a minimum amount of fear, stress, and/or pain in any combination) alone, or a determination that the patient exhibits skin discoloration alone.

In another aspect, the system may also be tuned to require any two of the four determinations (presence of edema, pupil dilation, emotional pressure, skin discoloration) from the image analysis. In another aspect, the system may also be tuned to require any three of the four determinations from the image analysis. In another aspect, the system may be turned to require that all four of the determinations be made in order to determine that cardiac failure in the patient is worsening. It should be appreciated that the greater number of items such as edema, pupil dilation, and emotional pressure found in the patient result in greater accuracy in the determination that cardiac failure in the patient is worsening.

In one or more other embodiments, one or more of the image processing techniques described herein may be used independently of the method described with reference to FIG. 2. For instance, the example methods described herein in connection with FIGS. 12, 13, 14, and/or 15 may be performed independently or in combination with one another to detect, measure, and/or assess edema, pupil dilation, emotional state, and/or skin discoloration as the case may be. As such, the methods may be performed in response to a received command to do so and/or in response to another triggering event.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise. As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without patient or user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory elements, as described herein, are examples of a computer readable storage medium. A non-exhaustive list of more specific examples of a computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, or the like.

As defined herein, the terms "one embodiment," "an embodiment," "one or more embodiments," or similar language mean that a particular feature, structure, or characteristic described in connection with the embodiment is included in at least one embodiment described within this disclosure. Thus, appearances of the phrases "in one embodiment," "in an embodiment," "in one or more embodiments," and similar language throughout this disclosure may, but do not necessarily, all refer to the same embodiment. The terms "embodiment" and "arrangement" are used interchangeably within this disclosure.

As defined herein, the term "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process.

As defined herein, the term "patient" means a human being undergoing medical treatment for a condition. In one aspect, a patient is a human being with heart failure. As defined herein, the term "user" means a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object oriented programming language and/or procedural programming languages. Computer readable program instructions may specify state-setting data. The computer readable program instructions may execute entirely on the patient's computer, partly on the patient's computer, as a stand-alone software package, partly on the patient's computer and partly on a remote computer or entirely on the remote computer or server. In the latter scenario, the remote computer may be connected to the patient's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. An apparatus for assessing heart failure, comprising:
an image sensor configured to capture image data of a patient;
a sensor configured to capture sensor data for the patient;
a memory configured to store the image data and the sensor data; and
a processor coupled to the image sensor, the sensor, and the memory, wherein the processor is configured to:
receive image data in response to detecting a biological condition from the sensor data, wherein the biological condition is indicative of psychophysiological health and cardiac health;

detect a visual characteristic from the image data, wherein the visual characteristic is indicative of heart health; and in response to detecting the visual characteristic, provide an indication that the patient is experiencing a worsening of heart failure.

2. The apparatus of claim 1, wherein the visual characteristic indicates edema.

3. The apparatus of claim 2, wherein the visual characteristic indicates size of an eye of the patient.

4. The apparatus of claim 2, wherein the processor is further configured to:

determine a body part of the patient as a candidate for the edema based upon detected activity of the patient from the sensor data; and prompt the patient to capture image data of the body part.

5. The apparatus of claim 2, wherein the processor is configured to:

generate a morphable model of a body part of the patient from the image data; and determine geometric characteristics of pitting in the body part based upon a deformation to the morphable model specified by an input.

6. The apparatus of claim 1, wherein the visual characteristic includes skin color.

7. The apparatus of claim 1, wherein the visual characteristic includes pupil dilation.

8. The apparatus of claim 1, wherein the visual characteristic includes a facial feature of the patient indicating emotional state.

9. The apparatus of claim 1, wherein the biological condition includes chronotropic incompetence.

10. The apparatus of claim 1, wherein the biological condition includes deterioration in ventilation threshold.

11. The apparatus of claim 1, wherein the biological condition includes stress.

12. The apparatus of claim 1, wherein the biological condition includes depression.

13. A method for assessing heart failure, comprising:

processing, using a processor, sensor data for a patient obtained from a sensor to detect a biological condition, wherein the biological condition is indicative of psychophysiological health and cardiac health;

receiving, using the processor, image data in response to detecting the biological condition from the sensor data;

detecting, using the processor, a visual characteristic from the image data, wherein the visual characteristic is indicative of heart health; and in response to detecting the visual characteristic, providing, using the processor, an indication that the patient is experiencing a worsening of heart failure.

14. The method of claim 13, wherein the visual characteristic indicates edema.

15. The method of claim 14, wherein the visual characteristic indicates size of an eye of the patient.

16. The method of claim 14, further comprising:

determining a body part of the patient as a candidate for the edema based upon detected activity of the patient from the sensor data; and prompting the patient to capture image data of the body part.

17. The method of claim 14, further comprising:

generating a morphable model of a body part of the patient from the image data; and determining geometric characteristics of pitting in the body part based upon a deformation to the morphable model specified by an input.

18. The method of claim 13, wherein the visual characteristic includes skin color.

19. The method of claim 13, wherein the visual characteristic includes pupil dilation.

20. The method of claim 13, wherein the visual characteristic includes a facial feature of the patient indicating emotional state.

21. The method of claim 13, wherein the biological condition includes chronotropic incompetence.

22. The method of claim 13, wherein the biological condition includes deterioration in ventilation threshold.

23. The method of claim 13, wherein the biological condition includes stress.

24. The method of claim 13, wherein the biological condition includes depression.

25. A computer program product comprising a computer readable storage medium having program code stored thereon for assessing heart failure, the program code executable by a processor to perform operations comprising:

processing sensor data for a patient obtained from a sensor to detect a biological condition, wherein the biological condition is indicative of psychophysiological health and cardiac health;

receiving image data in response to detecting the biological condition from the sensor data;

detecting a visual characteristic from the image data, wherein the visual characteristic is indicative of heart health; and in response to detecting the visual characteristic, providing an indication that the patient is experiencing a worsening of heart failure.

26. The computer program product of claim 25, wherein the visual characteristic indicates edema.

27. The computer program product of claim 26, wherein the visual characteristic indicates size of an eye of the patient.

28. The computer program product of claim 26, wherein the program code is executable by the processor to perform operations further comprising:

determining a body part of the patient as a candidate for the edema based upon detected activity of the patient from the sensor data; and prompting the patient to capture image data of the body part.

29. The computer program product of claim 26, wherein the program code is executable by the processor to perform operations further comprising:

generating a morphable model of a body part of the patient from the image data; and determining geometric characteristics of pitting in the body part based upon a deformation to the morphable model specified by an input.

30. The computer program product of claim 25, wherein the visual characteristic includes skin color.

31. The computer program product of claim 25, wherein the visual characteristic includes pupil dilation.

32. The computer program product of claim 25, wherein the visual characteristic includes a facial feature of the patient indicating emotional state.

33. The computer program product of claim 25, wherein the biological condition includes chronotropic incompetence.

34. The computer program product of claim 25, wherein the biological condition includes deterioration in ventilation threshold.

35. The computer program product of claim 25, wherein the biological condition includes stress.

36. The computer program product of claim 25, wherein the biological condition includes depression.

37. An apparatus for assessing heart failure, comprising:
an image sensor configured to capture image data;
a memory configured to store the image data; and
a processor coupled to the image sensor and the memory, wherein the processor is configured to:
generate a morphable model based upon image data for a selected part of a patient's body;
receive a user specified deformation to the morphable model, wherein deformation approximates an amount of pitting experienced by the patient for the selected part of the patient's body; and
determine severity of edema experienced by the patient based upon the deformation to the morphable model.

38. The apparatus of claim 37, wherein the processor is configured to:
determine a rate at which pitting in the selected part of the patient's body rebounds using the morphable model.

39. The apparatus of claim 37, wherein the processor is configured to:
determine a rate at which pitting in the selected part of the patient's body rebounds based upon image analysis of further image data of the part of the patient's body.

40. The apparatus of claim 37, wherein the processor is configured to:
determine a dilation ratio of a pupil of the patient based upon extracted contours of an iris of the patient and the pupil of the patient from the image data; and
determine an amount of deviation in pupil dilation of the patient based upon a comparison of the dilation ratio with a reference dilation ratio.

* * * * *